US012714740B2

(12) United States Patent
Yurek et al.

(10) Patent No.: US 12,714,740 B2
(45) Date of Patent: Aug. 25, 2026

(54) COMPOSITIONS COMPRISING A TWEAK LIGAND AND METHODS OF USING SAME

(71) Applicants: Children's Hospital Medical Center, Cincinnati, OH (US); University of Cincinnati, Cincinnati, OH (US); University of Kentucky Research Foundation, Lexington, KY (US)

(72) Inventors: David Yurek, Lexington, KY (US); Kim B. Seroogy, Loveland, OH (US); Assem Ziady, Cincinnati, OH (US)

(73) Assignees: Children's Hospital Medical Center, Cincinnati, OH (US); UNIVERSITY OF CINCINNATI, Cincinnati, OH (US); University of Kentucky Research Foundation, Lexington, KY (US)

( * ) Notice: Subject to any disclaimer, the term of this patent is extended or adjusted under 35 U.S.C. 154(b) by 1178 days.

(21) Appl. No.: 17/604,557

(22) PCT Filed: Apr. 29, 2020

(86) PCT No.: PCT/US2020/030401

§ 371 (c)(1),
(2) Date: Oct. 18, 2021

(87) PCT Pub. No.: WO2020/223302

PCT Pub. Date: Nov. 5, 2020

(65) Prior Publication Data

US 2022/0202902 A1 Jun. 30, 2022

Related U.S. Application Data

(60) Provisional application No. 62/839,970, filed on Apr. 29, 2019.

(51) Int. Cl.

| | |
|---|---|
| ***A61K 38/19*** | (2006.01) |
| ***A61K 9/16*** | (2006.01) |
| ***A61K 31/4545*** | (2006.01) |
| ***A61K 31/513*** | (2006.01) |
| ***A61K 31/522*** | (2006.01) |
| ***A61K 38/45*** | (2006.01) |
| ***A61K 38/48*** | (2006.01) |
| ***A61K 38/51*** | (2006.01) |
| ***A61K 47/42*** | (2017.01) |
| ***A61K 48/00*** | (2006.01) |

(52) U.S. Cl.

CPC .......... *A61K 38/191* (2013.01); *A61K 9/1641* (2013.01); *A61K 31/4545* (2013.01); *A61K 31/513* (2013.01); *A61K 31/522* (2013.01); *A61K 38/45* (2013.01); *A61K 38/4873* (2013.01); *A61K 38/51* (2013.01); *A61K 47/42* (2013.01); *A61K 48/0058* (2013.01)

(58) Field of Classification Search

None

See application file for complete search history.

(56) References Cited

U.S. PATENT DOCUMENTS

| | | | |
|---|---|---|---|
| 4,208,479 | A | 6/1980 | Zuk et al. |
| 7,741,038 | B2 | 6/2010 | Sarwal et al. |
| 8,017,577 | B2 | 9/2011 | Cooper et al. |
| 8,911,786 | B2 | 12/2014 | Desai et al. |
| 9,018,179 | B2 | 4/2015 | Kay et al. |
| 9,993,494 | B2 | 6/2018 | Appleman et al. |
| 10,126,295 | B2 | 11/2018 | Saavedra |
| 10,300,143 | B2 | 5/2019 | Sengupta et al. |
| 10,654,910 | B2 | 5/2020 | Spencer et al. |
| 10,761,099 | B2 | 9/2020 | Ziady et al. |
| 10,894,960 | B2 | 1/2021 | Ziady et al. |
| 2006/0142225 | A1 | 6/2006 | McSwiggen |
| 2006/0148828 | A1 | 7/2006 | Gianella-Borradori et al. |
| 2006/0153808 | A1 | 7/2006 | Cristofanilli et al. |
| 2006/0292562 | A1 | 12/2006 | Pollard et al. |

(Continued)

FOREIGN PATENT DOCUMENTS

| | | | |
|---|---|---|---|
| AU | 2013270447 | A1 | 1/2014 |
| WO | 2009/038913 | A2 | 3/2009 |

(Continued)

OTHER PUBLICATIONS

Huang L, et al. Highly Selective Targeting of Hepatic Stellate Cells for Liver Fibrosis Treatment Using a d-Enantiomeric Peptide Ligand of Fn14 Identified by Mirror-Image mRNA Display. Mol Pharm. May 1, 2017;14(5):1742-1753. doi: 10.1021/acs.molpharmaceut.6b01174. Epub Apr. 12, 2017. PMID: 28358987. (Year: 2017).*

Kurihara et al. Glioma/glioblastoma-specific adenoviral gene expression using the nestin gene regulator. Gene Ther. Apr. 2000;7(8):686-93. doi: 10.1038/sj.gt.3301129. PMID: 10800092. (Year: 2000).*

Voges et al. Imaging-guided convection-enhanced delivery and gene therapy of glioblastoma. Ann Neurol. Oct. 2003;54(4):479-87. doi: 10.1002/ana.10688. PMID: 14520660. (Year: 2003).*

(Continued)

*Primary Examiner* — Robert A Wax
*Assistant Examiner* — Julia A Rossi
(74) *Attorney, Agent, or Firm* — Nicole M. Tepe

(57) ABSTRACT

The instant disclosure relates to nanoparticle compositions that may be used for the targeting of certain cells or tissues. The nanoparticles may take a variety of different forms, including non-viral, viral, and lipid nanoparticles, and may utilize a TNF receptor superfamily member 12A ("TWEAKR") binding region of the TWEAK protein to target a nanoparticle to tissues expressing TWEAKR. The compositions may further comprise a suicide gene optionally under the control of a tissue specific promoter. In further aspects, methods of treating an individual using the disclosed nanoparticle compositions are described.

12 Claims, 4 Drawing Sheets

(56) References Cited

U.S. PATENT DOCUMENTS

| | | | |
|---|---|---|---|
| 2008/0133141 | A1 | 6/2008 | Frost |
| 2012/0128782 | A1 | 5/2012 | Green et al. |
| 2013/0143752 | A1 | 6/2013 | Edmiston et al. |
| 2017/0042819 | A1 | 2/2017 | Goomer |
| 2017/0314074 | A1 | 11/2017 | Kossen et al. |
| 2017/0360749 | A1 | 12/2017 | Harijith et al. |
| 2018/0009873 | A1 | 1/2018 | Spencer et al. |
| 2019/0128901 | A1 | 5/2019 | Cozma |
| 2020/0341009 | A1 | 10/2020 | Ziady et al. |
| 2021/0102208 | A1 | 4/2021 | Ziady et al. |
| 2021/0302439 | A1 | 9/2021 | Ziady et al. |
| 2023/0330121 | A1 | 10/2023 | Ziady et al. |
| 2023/0416782 | A1 | 12/2023 | Ziady et al. |
| 2024/0066021 | A1 | 2/2024 | Ziady et al. |
| 2024/0103017 | A1 | 3/2024 | Hardie et al. |

FOREIGN PATENT DOCUMENTS

| | | | |
|---|---|---|---|
| WO | 2009/055671 | A1 | 4/2009 |
| WO | 2011/038901 | A1 | 4/2011 |
| WO | 2015/157546 | A1 | 10/2015 |
| WO | 2018/208849 | A1 | 11/2018 |
| WO | 2021/053058 | A1 | 3/2021 |
| WO | 2022/031877 | A1 | 2/2022 |

OTHER PUBLICATIONS

Kim et al. (2012). Non-degradative intracellular trafficking of highly compacted polymeric DNA nanoparticles. Journal of controlled release : official journal of the Controlled Release Society, 158(1), 102-107. https://doi.org/10.1016/j.jconrel.2011.10.031 (Year: 2012).*

Schneider et al. Minimizing the non-specific binding of nanoparticles to the brain enables active targeting of Fn14-positive glioblastoma cells. Biomaterials. Feb. 2015;42:42-51. doi: 10.1016/j.biomaterials.2014.11.054. Epub Dec. 13, 2014. PMID: 25542792; PMCID: PMC4279109. (Year: 2014).*

Zhou et al. Development of human serine protease-based therapeutics targeting Fn14 and identification of Fn14 as a new target overexpressed in TNBC. Mol Cancer Ther. Nov. 2014;13(11):2688-705. doi: 10.1158/1535-7163. (Year: 2014).*

Zhang et al. (2017). Strategies to enhance the distribution of nanotherapeutics in the brain. Journal of controlled release : official journal of the Controlled Release Society, 267, 232-239. https://doi.org/10.1016/j.jconrel.2017.07.028 (Year: 2017).*

Miller et al. Radiation Therapy Primes Tumors for Nanotherapeutic Delivery via Macrophage-Mediated Vascular Bursts. Sci. Transl. Med. 2017, 9, eaal0225 DOI: 10.1126/scitranslmed.aal0225 (Year: 2017).*

Altieri, D.C., “Validating Survivin as a Cancer Therapeutic Target,” Nat Rev Cancer, 2003, 3(1):46-54, 9 pgs.

Arai, H., et al., “Nestin expression in brain tumors: its utility for pathological diagnosis and correlation with the prognosis of high-grade gliomas,” Brain Tumor Pathol, 2012, 29(3):160-167, 8 pgs.

Assi, H., et al., “Gene Therapy for Brain Tumors: Basic Developments and Clinical Implementation,” Neurosci Lett, 2012, 527(2):71-77, 14 pgs.

Bhang, H.-E.C., et al., “Tumor-Specific Imaging Through Progression Elevated Gene-3 Promoter-Driven Gene Expression,” Nat Med, 2011, 17(1):123-129, 16 pgs.

Bossen, C., et al., “Interactions of Tumor Necrosis Factor (TNF) and TNF Receptor Family Members in the Mouse and Human,” J Biol Chem, 2006, 281(20):13964-13971, 8 pgs.

Chen, X., et al., “Cell Surface Nucleolin Serves as Receptor for DNA Nanoparticles Composed of Pegylated Polylysine and DNA,” Mol Ther, 2008, 16(2):333-342, 10 pgs.

Chen, X., et al., “Nucleolin-Mediated Cellular Trafficking of DNA Nanoparticle Is Lipid Raft and Microtubule Dependent and Can Be Modulated by Glucocorticoid,” Mol Ther, 2011, 19(1):93-102, 10 pgs.

Christensen, C.L., et al., “Targeted cytosine deaminase-uracil phosphoribosyl transferase suicide gene therapy induces small cell lung cancer-specific cytotoxicity and tumor growth delay,” Clin Cancer Res, 2010, 16(8):2308-2319, 21 pgs.

Dachs, G.U., et al, “From bench to bedside for gene-directed enzyme prodrug therapy of cancer,” Anti-Cancer Drugs, 2005, 16(4):349-359, 11 pgs.

Debinski, W., et al., “Convection-enhanced delivery for the treatment of brain tumors,” Expert Rev Neurother, 2009, 9(10):1519-1527, 15 pgs.

Fan, X., et al., “hTERT Gene Amplification and Increased mRNA Expression in Central Nervous System Embryonal Tumors,” Am J Pathol, 2003, 162(6):1763-1769, 7 pgs.

Fortin, S.P., et al., “Tumor Necrosis Factor-Like Weak Inducer of Apoptosis (TWEAK) Stimulation of Glioma Cell Survival Is Dependent Upon Akt2 Function,” Mol Cancer Res, 2009, 7(11):1871-1881, 24 pgs.

Galzio, R., et al., “Glycosilated Nucleolin as Marker for Human Gliomas,” J Cell Biochem, 2012, 113(2):571-579, 9 pgs.

Gurunathan, S., et al., “Regulation of Fibroblast Growth Factor-inducible 14 (Fn14) Expression Levels via Ligand-independent Lysosomal Degradation,” J Biol Chem, 2014, 289(19):12976-12988, 13 pgs.

Han, Z., et al., “AAV and Compacted DNA Nanoparticles for the Treatment of Retinal Disorders: Challenges and Future Prospects,” Invest Ophthalmol Vis Sci, 2011, 52(6):3051-3059, 9 pgs.

Haung, L., et al., “Highly Selective Targeting of Hepatic Stellate Cells for Liver Fibrosis Treatment Using a D-Enantiomeric Peptide Ligand of Fn14 Identified by Mirror-Image mRNA Display,” Mol Pharmaceutics, 2017, 14:1742-1753, 12 pgs.

Hersh, D.S., et al., “The TNF receptor family member Fn14 is highly expressed in recurrent glioblastoma and in GBM patient-derived xenografts with acquired temozolomide resistance,” Neuro Oncol, 2018, 20(10):1321-1330, 10 pgs.

Jiang, X., et al., “The Imprinted Gene PEG3 Inhibits Wnt Signaling and Regulates Glioma Growth,” J Biol Chem, 2010, 285(11):8472-8480, 9 pgs.

Joo, K.M., et al., “Patient-Specific Orthotopic Glioblastoma Xenograft Models Recapitulate the Histopathology and Biology of Human Glioblastomas In Situ,” Cell Rep, 2013, 3(1):260-273, 14 pgs.

Kajiwara, Y., et al., “Expression of Survivin in Astrocytic Tumors: Correlation with Malignant Grade and Prognosis,” Cancer, 2003, 97(4):1077-1083, 7 pgs.

Kibbey, M.C., et al., “A 110-kD Nuclear Shuttling Protein, Nucleolin, Binds to the Neurite-Promoting IKVAV Site of Laminin-1,” J Neurosci Res, 1995, 42(3):314-322, 9 pgs.

Konstan, M.W., et al., “Compacted DNA nanoparticles administered to the nasal mucosa of cystic fibrosis subjects are safe and demonstrate partial to complete cystic fibrosis transmembrane regulator reconstitution,” Hum. Gene Ther., Dec. 2004, 15(12):1255-69, 15 pgs.

Li, A., et al., “Unsupervised Analysis of Transcriptomic Profiles Reveals Six Glioma Subtypes,” Cancer Res, 2009, 69(5):2091-2099, 17 pgs.

Liu, G., et al., “Nanoparticles of Compacted DNA Transfect Postmitotic Cells,” J Biol Chem, 2003, 278(35):32578-32586, 9 pgs.

Martens, T., et al., “Inhibition of Glioblastoma Growth in a Highly Invasive Nude Mouse Model Can Be Achieved by Targeting Epidermal Growth Factor Receptor but not Vascular Endothelial Growth Factor Receptor-2,” Clin Cancer Res, 2008, 14(17):5447-5458, 12 pgs.

Mastorakos, P., et al., “Highly PEGylated DNA Nanoparticles Provide Uniform and Widespread Gene Transfer in the Brain,” Adv Healthc Mater, 2015, 4(7):1023-1033, 24 pgs.

Mead, B.P., et al., “Novel Focused Ultrasound Gene Therapy Approach Noninvasively Restores Dopaminergic Neuron Function in a Rat Parkinson's Disease Model,” Nano Lett, 2017, 17(6):3533-3542, 21 pgs.

Nance, E.A., et al., “A Dense Poly(ethylene glycol) Coating Improves Penetration of Large Polymeric Nanoparticles within Brain Tissue,” Sci Transl Med, 2012, 4(149):149ra119, 18 pgs.

Ndesendo, V.M., “Convection-Enhanced Delivery of Neurotherapeutics,” In: V. Pillay and Y.E. Choonara, (Eds.), *Advances*

(56) References Cited

OTHER PUBLICATIONS

*in Neurotherapeutic Delivery Technologies*, vol. 8, UK: Omics International, 2015, https://doi.org/10.4172/978-1-63278-036-2-037, www.esciencecentral.org/ebooks, 3 pgs. (Bibliographic information only).

Neeves, K.B., et al., "Dilation and degradation of the brain extracellular matrix enhances penetration of infused polymer nanoparticles," Brain Res, 2007, 1180:121-132, 23 pgs.

Negroni, L., et al., "Treatment of colon cancer cells using the cytosine deaminase/5-fluorocytosine suicide system induces apoptosis, modulation of the proteome, and Hsp90β phosphorylation," Mol Cancer Ther, 2007, 6(10):2747-2756, 10 pgs.

O'Mahony, A.M., et al., "Non-viral Nanosystems for Gene and Small Interfering RNA Delivery to the Central Nervous System: Formulating the Solution," J Pharm Sci, 2013, 102(10):3469-3484, 16 pgs.

Ostrom, Q.T., et al., "CBTRUS Statistical Report: Primary Brain and Central Nervous System Tumors Diagnosed in the United States in 2006-2010," Neuro-Oncol, 2013, 15(Suppl 2):ii1-ii56, 56 pgs.

Patrizii, M., et al., "Utility of Glioblastoma Patient-Derived Orthotopic Xenografts in Drug Discovery and Personalized Therapy," Front Oncol, 2018, 8:article 23, 9 pgs.

Pelekanou, V., et al., "Baff, April, TWEAK, BCMA, TACI and Fn14 Proteins Are Related to Human Glioma Tumor Grade: Immunohistochemistry and Public Microarray Data Meta-Analysis," PLoS One, 2013, 8(12):e83250, 11 pgs.

Perez, J.G., et al., "The TWEAK Receptor Fn14 is a Potential Cell Surface Portal for Targeted Delivery of Glioblastoma Therapeutics," Oncogene, 2016, 35(17):2145-2155, 27 pgs.

Phillips, H.S., et al., "Molecular subclasses of high-grade glioma predict prognosis, delineate a pattern of disease progression, and resemble stages in neurogenesis," Cancer Cell, 2006, 9(3):157-173, 17 pgs.

Portsmouth, D., et al., "Suicide genes for cancer therapy," Mol Aspects Med, 2007, 28(1):4-41, 38 pgs.

Redgate, E.S., et al., "Time of Death of CNS Tumor-Bearing Rats Can Be Reliably Predicted by Body Weight-Loss Patterns," Lab Anim Sci, 1991, 41(3):269-273, 5 pgs.

Saucier-Sawyer, J.K., et al., "Distribution of Polymer Nanoparticles by Convection-Enhanced Delivery to Brain Tumors," J Control Release, 2016, 232:103-112, 26 pgs.

Sausville, E.A. et al, "Contributions of Human Tumor Xenografts to Anticancer Drug Development," Cancer Res, 2006, 66(7):3351-3354, discussion 3354, 4 pgs.

Schwartzbaum, J.A., et al., "Epidemiology and molecular pathology of glioma," Nat Clin Pract Neurol, 2006, 2(9):494-503, 10 pgs.

Shirahata, M., et al., "Gene Expression-Based Molecular Diagnostic System for Malignant Gliomas Is Superior to Histological Diagnosis," Clin Cancer Res, 2007, 13(24):7341-7356, 16 pgs.

Shirahata, M., et al., "Using gene expression profiling to identify a prognostic molecular spectrum in gliomas," Cancer Sci, 2009, 100(1):165-172, 8 pgs.

Shirakawa, T., et al., "Cytotoxicity of Adenoviral-Mediated Cytosine Deaminase Plus 5-Fluorocytosine Gene Therapy is Superior to Thymidine Kinase Plus Acyclovir in a Human Renal Cell Carcinoma Model," J Urol, 1999, 162(3 Pt 1):949-954, 6 pgs.

Soundararajan, S., et al., "Plasma Membrane Nucleolin Is a Receptor for the Anticancer Aptamer AS1411 in MV4-11 Leukemia Cells," Mol Pharmacol, 2009, 76(5):984-991, 8 pgs.

Sun, W., et al., "Real-Time Imaging of Gene Delivery and Expression with DNA Nanoparticle Technologies," Chapter 33 in James W. Lee and Robert S. Foote (eds.), *Micro and Nano Technologies in Bioanalysis*, Methods in Molecular Biology, 2009, 544:525-546, 22 pgs.

Taillandier, L., et al., "Models for neuro-oncological preclinical studies: solid orthotopic and heterotopic grafts of human gliomas into nude mice," J Neurosci Methods, 2003, 125(1-2):147-157, 11 pgs.

Tobias, A., et al., "The art of gene therapy for glioma: a review of the challenging road to the bedside," J Neurol Neurosurg Psychiatry, 2013, 84(2):213-222, 20 pgs.

Tran, N.L., et al., "Increased Fibroblast Growth Factor-Inducible 14 Expression Levels Promote Glioma Cell Invasion via Racl and Nuclear Factor-κB and Correlate with Poor Patient Outcome," Cancer Res, 2006, 66(19):9535-9542, 8 pgs.

Tran, N.L., et al., "The Human Fn14 Receptor Gene Is Up-Regulated in Migrating Glioma Cells in Vitro and Overexpressed in Advanced Glial Tumors," Am J Pathol, 2003, 162(4):1313-1321, 9 pgs.

Trinh, Q.T., et al., "Enzyme/Prodrug Gene Therapy: Comparison of Cytosine Deaminase/5-Fluorocytosine Versus Thymidine Kinase/Ganciclovir Enzyme/Prodrug Systems in a Human Colorectal Carcinoma Cell Line," Cancer Res, 1995, 55(21):4808-4812, 5 pgs.

Vogelbaum, M.A. et al., "Convection-enhanced delivery for the treatment of glioblastoma," Neuro-Oncol, 2015, 17(Suppl 2):ii3-ii8, 6 pgs.

Winkles, J.A., "The TWEAK-Fn14 cytokine-receptor axis: discovery, biology and therapeutic targeting," Nat Rev Drug Discov, 2008, 7(5):411-425, 32 pgs.

Workman, P., et al., "Guidelines for the welfare and use of animals in cancer research," Br J Cancer, 2010, 102(11):1555-1577, 23 pgs.

Xu, Z., et al., "Knocking down necleolin expression in gliomas inhibits tumor growth and induces cell cycle arrest," J Neurooncol, 2012, 108:59-67, 9 pgs.

Xu, Z., et al., "Orthotopic Patient-Derived Glioblastoma Xenografts in Mice," Methods Mol Biol, Ch. 14 in Dimitris G. Placantonakis (ed.), *Glioblastoma: Methods and Protocols*, Springer Science+Business Media, LLC, 2018, 1741:183-190, 8 pgs.

Yabroff, K.R., et al., "Patterns of care and survival for patients with glioblastoma multiforme diagnosed during 2006," Neuro-Oncol, 2012, 14(3):351-359, 9 pgs.

Yurek, D., et al., "Intracerebral injections of DNA nanoparticles encoding for a therapeutic gene provide partial neuroprotection in an animal model of neurodegeneration," Nanomedicine: Nanotechnology, Biology, and Medicine, 2017, 13(7):2209-2217, 9 pgs.

Yurek, D.M., et al., "Age and lesion-induced increases of GDNF transgene expression in brain following intracerebral injections of DNA nanoparticles," Neuroscience, 2015, 284:500-512, 28 pgs.

Yurek, D.M., et al., "Compacted DNA nanoparticle gene transfer of GDNF to the rat striatum enhances the survival of grafted fetal dopamine neurons," Cell Transplant, 2009, 18(10):1183-96, 15 pgs.

Yurek, D.M., et al., "DNA Nanoparticles: Detection of Long-term Transgene Activity in Brain Using Bioluminescence Imaging," Mol. Imaging, Apr. 26, 2011, 10(5):327-339, 12 pgs.

Yurek, D.M., et al., "Long-term transgene expression in the central nervous system using DNA nanoparticles," Mol. Ther., Apr. 2009, 17(4):641-50, 14 pgs.

Zarogoulidis, P., et al., "Suicide Gene Therapy for Cancer—Current Strategies," J Genet Syndr Gene Ther, 2013, 4, 29 pgs.

Zhang, J., et al., "Gene-Directed Enzyme Prodrug Therapy," AAPS J, 2015, 17(1):102-110, 9 pgs.

Zhou, H., et al., "Development of Human Serine Protease-Based Therapeutics Targeting Fn14 and Identification of Fn14 as a New Target Overexpressed in TNBC," Mol Cancer Ther, 2014, 13(11):2688-2705, 34 pgs.

Ziady, A.-G., et al., "Minimal Toxicity of Stabilized Compacted DNA Nanoparticles in the Murine Lung," Mol Ther, 2003, 8(6):948-956, 9 pgs.

Ziady, A.-G., et al., "Transfection of Airway Epithelium by Stable PEGylated Poly-$_L$-lysine DNA Nanoparticles in Vivo," Mol Ther, 2003, 8(6):936-947, 12 pgs.

Accurso FJ, et al., "Effect of VX-770 in Persons with Cystic Fibrosis and the G551D-CFTR Mutation." N Engl J Med, Nov. 18, 2010, 363(21):1991-2003, 13 pgs.

Ahmed, H., et al., "Emerging Gene Therapies for Genetic Hearing Loss," J Assoc Res Otolaryngol, Aug. 16, 2017, 22 pgs.

Albert PS, et al., "An Approach For Jointly Modeling Multivariate Longitudinal Measurements And Discrete Time-To-Event Data," Ann Appl Stat, 2010, 4(3):1517-1532, 16 pgs.

(56) References Cited

OTHER PUBLICATIONS

Asar O, et al., "mmm: An R package for analyzing multivariate longitudinal data with multivariate marginal models," Comput Methods Programs Biomed, 2013, 112(3):649-654, 6 pgs.
Brebner JA, et al., "Polyclonal free light chains: a biomarker of inflammatory disease or treatment target?" F1000 Med Rep, 2013, 5:4, 6 pgs.
Brody, A.S., et al., "High-Resolution Computed Tomography in Young patients with Cystic Fibrosis: Distribution of Abnormalities and Correlation with Pulmonary Function Tests," J Peds, 2004, 145(1):32-38, 7 pgs.
Bundgaard, H., (ed.), *Design of Prodrugs*, Elsevier, Amsterdam, 1985, pp. 7-9, 21-24, 8 pgs.
Cai, X., et al., "Gene delivery to mitotic and postmitotic photoreceptors via compacted DNA nanoparticles results in improved phenotype in a mouse model of retinitis pigmentosa," Faseb J, Apr. 2010, 24(4):1178-91, 25 pgs.
Chassagnon, G., et al., "Long-term computed tomographic changes in cystic fibrosis patients treated with ivacaftor," Eur Respir J, 2016, 48(1):249-252, 4 pgs.
Chatterjee N, et al., "Constrained Maximum Likelihood Estimation for Model Calibration Using Summary-level Information from External Big Data Sources" J Am Stat Assoc, 2016, 111(513):107-117, 11 pgs.
Chen J, et al., "Dysfunction of Nrf-2 in CF Epithelia Leads to Excess Intracellular $H_2O_2$ and Inflammatory Cytokine Production," PLoS One, 2008, 3(10):e3367, 12 pgs.
Chipman Ha, et al., "BART: Bayesian Additive Regression Trees," Ann Appl Stat, 2014, 23(1):42-59, 33 pgs.
Chirkova T, et al., "CX3CR1 is an important surface molecule for respiratory syncytial virus infection in human airway epithelial cells," J Gen Virol, 2015, 96:2543-2556, 14 pgs.
Chmiel J, et al., "The Effect of Sulforaphane In Broccoli Sprouts On Nrf2 Activation, Glutathione, Markers of Oxidative Stress, and Neutrophil Migration," Pediatr Pulmonol, 2012, 47(S35):250; 2012 Cystic Fibrosis Conference, Poster Session Abstract 82*, 1 pg.
Chromy, B.A., et al., "Proteomic Analysis of Human Serum by Two-Dimensional Differential Gel Electrophoresis after Depletion of High-Abundant Proteins," Journal of Proteome Research, 2004, 3:1120-1127, 8 pgs.
Chui, CK, et al., "Interpolation by Multivariate Splines," Math Comput, 1988, 51(183):203-218, 16 pgs.
Clancy JP, et al., "Personalized Medicine in Cystic Fibrosis: Dawning of a New Era," Am J Respir Crit Care Med, 2012, 186(7):593-597, 5 pgs.
Deboer, E.M., et al., "Novel Application of Aptamer Proteomic Analysis in Cystic Fibrosis Bronchoalveolar Lavage Fluid," Proteomics Clin Appl, 2019, 13:1800085, 8 pgs.
Deboer, E.M., et al., "Proteomic profiling identifies novel circulating markers associated with bronchiectasis in cystic fibrosis," Proteomics Clin Appl, 2017, 11(9-10):1600147, 9 pgs.
Diggle PJ, et al., "Real-time monitoring of progression towards renal failure in primary care patients," Biostatistics, 2015, 16(3):522-536, 15 pgs.
Ding, X.Q., et al., "Ocular delivery of compacted DNA-nanoparticles does not elicit toxicity in the mouse retina," PLoS One, 2009, 4(10):e7410, 11 pgs.
Drumm ML, et al., "Genetic Variation and Clinical Heterogeneity in Cystic Fibrosis," Annu Rev Pathol, 2012, 7:267-282, 18 pgs.
Duan LL, et al., "Joint Hierarchical Gaussian Process Model with Application to Forecast in Medical Monitoring," 2014, eprint arXiv:1408.4660, 23 pgs.
Duan LL, et at., "Bayesian Ensemble Trees (BET) for Clustering and Prediction in Heterogeneous Data," J Comput Graph Stat, 2016, 25(3):748-761, 14 pgs.
Eichinger, M., et al., "Morphologic and functional scoring of cystic fibrosis lung disease using MRI," European Journal of Radiology, 2012, 81(6):1321-1329, 9 pgs.
Fagerland, M.W., et al., "The McNemar test for binary matched-pairs data: mid-p and asymptotic are better than exact conditional," BMC Med Res Methodol, 2013, 13:91, 8 pgs.
Farjo, R., et al., "Efficient non-viral ocular gene transfer with compacted DNA nanoparticles," PLoS One, 2006, 1:e38, 12 pgs.
Feng, S., et al., "Recombinant adenoviral vector expressing human wild-type p53, GM-CSF, and B7-1 genes suppresses the growth of glioma in vivo," Tumor Biol, 2014, 35:441-4417, 7 pgs.
Fieuws S, et al., "Predicting renal graft failure using multivariate longitudinal profiles," Biostatistics, 2008, 9(3):419-431, 13 pgs.
Fieuws S, et al., "Random-effects models for multivariate repeated measures," Stat Methods Med Res, Oct. 2007, 16(5):387-397, 11 pgs.
Fischer K, et al., "Biomarker Profiling by Nuclear Magnetic Resonance Spectroscopy for the Prediction of All-Cause Mortality: An Observational Study of 17,345 Persons," PLoS Med, Feb. 2014, 11(2):e1001606, 12 pgs.
Fletcher, A.M., et al., "Transgene expression in the striatum following intracerebral injections of DNA nanoparticles encoding for human glial cell line-derived neurotrophic factor," Neuroscience, Oct. 27, 2011, 194:220-6, 7 pgs.
Green, PJ, et al., "Nonparametric regression and generalized linear models: a roughness penalty approach," 1st ed. London, New York: Chapman & Hall, 1994, ix, 182 p. Table of Contents Only, 8 pgs.
Groot Kormelink, T., et al., "Immunoglobulin Free Light Chains Are Increased in Hypersensitivity Pneumonitis and Idiopathic Pulmonary Fibrosis," PLoS one, 2011, 6(9):e25392, 7 pgs.
Guo, J., et al., "Longitudinal free-breathing MRI measurement of murine lung physiology in a progressive model of lung fibrosis," J Appl Physio, 2019, 126(4):1138-1149, 12 pgs.
Hanania, N.A., et al., "Acute bronchodilator responsiveness and health outcomes in COPD patients in the UPLIFT trial," Respiratory Research, 2011, 12(1):6, 11 pgs.
Harun SN, et al., "A systematic review of studies examining the rate of lung function decline in patients with cystic fibrosis," Paediatr Respir Rev, 2016, 20:55-66, 12 pgs.
Hastie T, et al., *The Elements of Statistical Learning: Data Mining, Inference, and Prediction*, Second Ed., Springer Science + Business Media, LLC, New York, NY, 2009, (Table of Contents Only) 12 pgs.
Higano, N.S., et al., "Retrospective respiratory self-gating and removal of bulk motion in pulmonary UTE MRI of neonates and adults," Magn Reason Med, 2017, 77(3):1284-1295, 25 pgs.
Higuchi, T., and V. Stella (Eds.), *Pro-drugs as Novel Drug Delivery Systems*, ACS Symposium Series 14, American Chemical Society, Washington, D.C., 1975, 6 pgs. [Bibliographic data only].
Hoy, S.M., "Elexacaftor/Ivacaftor/Tezacaftor: First Approval," Drugs, 2019, 79(18):2001-2007, 7 pgs.
Huang, J., et al., "CRISPR Editing in Biological and Biomedical Investigation," J Cell Physiol, Aug. 8, 2017, 19 pgs.
Huang, L., et al., "Highly Selective Targeting of Hepatic Stellate Cells for Liver Fibrosis Treatment Using a D-Enantiomeric Peptide Ligand of Fn14 Identified by Mirror-Image mRNA Display," Mol Pharmaceutics, 2017, 14:1742-1753, 12 pgs.
James GM, et al., "Principal component models for sparse functional data," Biometrika, 2000, 87(3):587-602, 16 pgs.
Jiang C-R, et al., "Covariate Adjusted Functional Principal Components Analysis For Longitudinal Data," The Annals of Statistics, 2010, 38(2): 1194-1226, 34 pgs.
Kim PY, et al., "Identification of plasma Complement C3 as a potential biomarker for neuroblastoma using a quantitative proteomic approach," J Proteomics, 2014, 96:1-12, 12 pgs.
King, T.E., et al., "A Phase 3 Trial of Pirfenidone in Patients with Idiopathic Pulmonary Fibrosis," N Engl J Med, 2014, 370(22):2083-2092, 10 pgs.
Koirala, A., et al., "S/MAR-containing DNA nanoparticles promote persistent RPE gene expression and improvement in RPE65-associated LCA," Hum Mol Genet, Apr. 15, 2013, 22(8):1632-42, 11 pgs.
Kolodziej, M., et al., "Roscotirine has anti-proliferative and pro-apoptotic effects on glioblastoma cell lines: A pilot study," Oncology Reports, 2015, 34:1549-1556, 8 pgs.
Konstan, M.W., et al., "Assessment of safety and efficacy of long-term treatment with combination lumacaftor and ivacaftor

(56) References Cited

OTHER PUBLICATIONS therapy in patients with cystic fibrosis homozygous for the F508del-CFTR mutation (Progress): a phase 3, extension study," Lancet Respir Med, 2017, 5(2):107-118, 12 pgs.

La Rosa PS, et al., "Hypothesis Testing and Power Calculations for Taxonomic-Based Human Microbiome Data," PLoS One, 2012, 7(12):e52078, 13 pgs.

Laguna TA, et al., "Sputum Desmosine During Hospital Admission for Pulmonary Exacerbation in Cystic Fibrosis," Chest, Dec. 2009, 136(6):1561-1568, 8 pgs.

Lancioni CL, et al., "*Mycobacterium tuberculosis* Lipoproteins Directly Regulate Human Memory $CD4^{+}T$ Cell Activation via Toll-Like Receptors 1 and 2," Infect Immun, Feb. 2011, 79(2):663-673, 11 pgs.

Lederlin, M., et al., "Three-Dimensional Assessment of Lung Tissue Density Using a Clinical Ultrashort Echo Time at 3 Tesla: A Feasibility Study in Healthy Subjects," J Magn Reson Imag, 2014, 40(4):839-847, 9 pgs.

Li Q, et al., "Rv2468c, a novel *Mycobacterium tuberculosis* protein that costimulates human $CD4^{+}T$ cells through VLA-5," J Leukoc Biol, Feb. 2012, 91(2):311-20, 10 pgs.

Liou TG, et al., "Year-to-year changes in lung function in individuals with cystic fibrosis," J Cyst Fibros, 2010, 9(4):250-6, 7 pgs.

Loew, W., et al., "A Volume Saddle Coil for Hyperpolarized $^{129}Xe$ Lung Imaging," Proc Int Soc Magn Reson Med, 2015, 23:1507, 1 pg. [Abstract only].

Miller, G.W., et al., "Hyperpolarized $^{3}He$ lung ventilation imaging with $B_1$-inhomogeneity correction in a single breath-hold scan," MAGMA, 2004, 16(5):218-226, 9 pgs.

Naso, M.F., et al., "Adeno-Associated Virus (AAV) as a Vector for Gene Therapy," Bio Drugs, Jul. 1, 2017, 31:317-334, 18 pgs.

Nick JA, et al., "Blood mRNA biomarkers for detection of treatment response in acute pulmonary exacerbations of cystic fibrosis," Thorax, 2013, 68(10):929-937, 9 pgs.

Niedbalski, P.J., et al., "Mapping and correcting hyperpolarized magnetization decay with radial keyhole imaging," Magn Reson Med, 2019, 82:367-376, 10 pgs.

Obuchowski NA, et al., "Sample Size Determination for Diagnostic Accuracy Studies Involving Binormal ROC Curve Indices," Stat Med, 1997, 16(13):1529-1542, 14 pgs.

Pearce, M.S., et al., "Radiation exposure from CT scans in childhood and subsequent risk of leukaemia and brain tumours: a retrospective cohort study," Lancet, 2012, 380(9840):499-505, 7 pgs.

Peila, C., et al., "Effects of Holder pasteurization on the protein profile of human milk," Italian journal of Pediatrics, 2016, 42:36, 8 pgs.

Peng, J., Restricted MLE for Functional Principal Components Analysis (R package fpca) 2015. Available from: https://CRAN.R-project.org/package=fpca, 12 pgs.

Peng, J., et al., "A Geometric Approach to Maximum Likelihood Estimation of the Functional Principal Components From Sparse Longitudinal Data," J Comput Graph Stat, 2009, 18(4):995-1015, Technical Report 2007a, 87 pgs.

Pipe, J.G., et al., "A New Design and Rationale for 3D Orthogonally Oversampled k-Space Trajectories," Magn Reson Med, 2011, 66(5):1303-1311, 9 pgs.

Ramsay Jo, et al., *Functional data analysis*, Second Ed., Springer Science + Business Media, Inc., New York., NY, 2005, p. 426, (Table of Contents only) 13 pgs.

Ratjen F, et al., "Effect of Azithromycin on Systemic Markers of Inflammation in Patients With Cystic Fibrosis Uninfected With *Pseudomonas aeruginosa*," Chest, 2012, 142(5):1259- 1266, 8 pgs.

Roach, D.J., et al., "Ultrashort Echo-Time Magnetic Resonance Imaging Is a Sensitive Method for the Evaluation of Early Cystic Fibrosis Lung Disease," Ann Am Thorac Soc, 2016, 13(11):1923-1931, 9 pgs.

Robison, R.K., et al., "Three-Dimensional Ultrashort Echo-Time Imaging Using a FLORET Trajectory," Magn Reson Med, 2017, 78(3):1038-1049, 12 pgs.

Roche, E.B., (Ed.), *Bioreversible Carriers in Drug Design: Theory and Application*, American Pharmaceutical Association, 1987, Pergamon Press, New York, 4 pgs. [Table of Contents only].

Rosenfeld M, et al., "Baseline Characteristics and Factors Associated With Nutritional and Pulmonary Status at Enrollment in the Cystic Fibrosis EPIC Observational Cohort," Pediatr Pulmonol, 2010, 45(9):934-944, 11 pgs.

Rosenfeld M, et al., "Decline in Lung Function Does not Predict Future Decline in Lung Function in Cystic Fibrosis Patients," Pediatr Pulmonol, 2015, 50(9):856-862, 7 pgs.

Sagel SD, et al., "Effect of Treatment of Cystic Fibrosis Pulmonary Exacerbations on Systemic Inflammation," Ann Am Thorac Soc, 2015, 12(5):708-717, 10 pgs.

Sagel SD, et al., "Validation of Candidate Serum Protein and Lipid Markers of Disease Severity In CF," Pediatr Pulmonol, 2014, 49(S38):288, 2014 Cystic Fibrosis Conference, Poster Session Abstract 205*, 1 pg.

Sanders DB, et al., "Failure to Recover to Baseline Pulmonary Function after Cystic Fibrosis Pulmonary Exacerbation," Am J Respir Crit Care Med, 2010, 182(5):627-632, 6 pgs.

Sawicki, G.S., et al., "Sustained Benefit from Ivacaftor Demonstrated by Combining Clinical Trial and Cystic Fibrosis Patient Registry Data," Am J Respir Crit Care Med, 2015, 192(7):836-842, 7 pgs.

Schluchter MD, et al., "Classifying Severity of Cystic Fibrosis Lung Disease Using Longitudinal Pulmonary Function Data," Am J Respir Crit Care Med, 2006, 174(7):780-786, 7 pgs.

Sinha C, et al., "Capturing the Direct Binding of CFTR Correctors to CFTR by Using Click Chemistry," Chembiochem, 2015, 16:2017-2022, 6 pgs.

Sinha C, et al., "PKA and actin play critical roles as downstream effectors in MRP4-mediated regulation of fibroblast migration," Cell Signal, 2015, 27(7):1345-1355, 11 pgs.

Slobodianik NH, et al., "Inflammatory biomarker profile in children with cystic fibrosis: preliminary study," Proc Nutr Soc, 3rd International Immunonutrition Workshop; Session 4: Dietary strategies to prevent and mitigate inflammatory diseases, 2010, 69(3):354-356, 3 pgs.

Stanojevic, S., et al., "Physiologic endpoints for clinical studies for cystic fibrosis," J Cyst Fibros, 2016, 15(4):416-423, 8 pgs.

Szczesniak RD, et al., "A semiparametric approach to estimate rapid lung function decline in cystic fibrosis," Annals of Epidemiology, 2013, 23(12):771-777, 7 pgs.

Szczesniak RD, et al., "Phenotypes of Rapid Cystic Fibrosis Lung Disease Progression during Adolescence and Young Adulthood," American Journal of Respiratory and Critical Care Medicine, 2017, 196(4): 471-478, 8 pgs.

Szczesniak, RD, et al., "Predicting Future Lung Function Decline in Cystic Fibrosis Patients: Statistical Methods and Clinical Connections," Pediatr Pulmonol, Letter to the Editor, 2016, 51(2):217-218, 2 pgs.

Szczesniak, R., et al., "Use of $FEV_1$ in Cystic Fibrosis Epidemiologic Studies and Clinical Trials: A Statistical Perspective for the Clinical Researcher," J Cyst Fibros, 2017, 16(3):318-326, 17 pgs.

Szczesniak, R.D., et al., "Dynamic predictive probabilities to monitor rapid cystic fibrosis disease progression," Statistics in Medicine, 2020, 39(6):740-756, 17 pgs.

Szczesniak, R.D., et al., "Improving Detection of Rapid Cystic Fibrosis Disease Progression—Early Translation of a Predictive Algorithm Into a Point-of-Care Tool" IEEE Journal of Translational Engineering in Health and Medicine, Point-of-Care Technologies, 2019, 7:2800108, 8 pgs.

Tang Y, et al., "Developing Adaptive Personalized Therapy for Cystic Fibrosis Using Reinforcement Learning," Submitted to Ann Appl Stat, 2012, 28 pgs.

Taylor-Robinson D, et al., "Understanding the natural progression in $\%FEV_1$ decline in patients with cystic fibrosis: a longitudinal study," Thorax, 2012, 67(10):860-866, 7 pgs.

Tepper, L.A., et al., "The development of bronchiectasis on chest computed tomography in children with cystic fibrosis: can pre-stages be identified?" Eur Radiol, 2016, 26(12):4563-4569, 7 pgs.

(56) References Cited

OTHER PUBLICATIONS

Thomen, R.P., et al., "Hyperpolarized $^{129}$Xe for investigation of mild cystic fibrosis lung disease in pediatric patients," J Cyst Fibros, 2017, 16(2):275-282, 8 pgs.
Tibshirani RJ., "Regression Shrinkage and Selection via the Lasso," J R Statist Soc B, 1996, 58(1):267-288, 22 pgs.
Tucholska M, et al., "Human Serum Proteins Fractionated by Preparative Partition Chromatography Prior to LC-ESI-MS/MS," J Proteome Res, 2009, 8(3):1143-1155, 13 pgs.
Verbeke G, et al., "The analysis of multivariate longitudinal data: A review," Stat Methods Med Res, 2014, 23(1):42-59, 18 pgs.
Vestbo, J., et al., "Natural history of COPD: Focusing on change in $FEV_1$," Respirology, 2016, 21(1):34-43, 10 pgs.
Wainwright CE, et al., "Lumacaftor-Ivacaftor in Patients with Cystic Fibrosis Homozygous for Phe508del CFTR," N Engl J Med, 2015, 373(3):220-231, 12 pgs.
Walkup, L.L., et al., "Feasibility, tolerability and safety of pediatric hyperpolarized $^{129}$Xe magnetic resonance imaging in healthy volunteers and children with cystic fibrosis," Pediatr Radiol, 2016, 46(12): 1651-1662, 23 pgs.
Walkup, L.L., et al., "Xenon-129 MRI detects ventilation deficits in pediatric stem-cell transplant patients unable to perform spirometry," Eur Respir J, 2019, 53(5):1-16, 16 pgs.
Wang J, et al., "Measuring the impact of apnea and obesity on circadian activity patterns using functional linear modeling of actigraphy data," J Circadian Rhythms, 2011, 9(1):11, 10 pgs.
Wang X, et al., "Hsp90 Cochaperone Aha1 Downregulation Rescues Misfolding of CFTR in Cystic Fibrosis," Cell, 2006, 127(4):803-815, 13 pgs.
Wielputz, M.O., et al., "Magnetic Resonance Imaging Detects Changes in Structure and Perfusion, and Response to Therapy in Early Cystic Fibrosis Lung Disease," Am J Respir Crit Care Med, 2014, 189(8):956-965, 10 pgs.
Wilcoxon, F., "Individual Comparisons of Grouped Data by Ranking Methods," Journal of Economic Entomology, 1946, 39(2):269-270, 2 pgs.
Willmering, M.M., et al., "Implementation of the FLORET Ultra-short Echo-Time Sequence for Lung Imaging," Magn Reson Med, 2019, 82(3):1091-1100, 17 pgs.
Willmering, M.M., et al., "Improved pulmonary $^{129}$Xe ventilation imaging via 3D-spiral UTE MRI," Magn Reson Med, 2020, 84(1):312-320, 14 pgs.
Wolff, M.E., (ed.), *Burger's Medicinal Chemistry and Drug Discovery*, 5th ed., 1995, pp. 172-178, 949-982, 41 pgs.
Yanagisawa K, et al., "Proteomic patterns of tumour subsets in non-small-cell lung cancer," Lancet, 2003, 362(9382):433-439, 7 pgs.
Yao, F., et al., "Functional Data Analysis for Sparse Longitudinal Data," Journal of the American Statistical Association, 2005, 100(470):577-590, 14 pgs.
Yu, J., et al., "Comparison of Lung $T_2$* During Free-Breathing at 1.5 T and 3.0 T with Ultrashort Echo Time Imaging," Magn Reson Med, 2011, 66(1):248-254, 7 pgs.
Zeitzer JM, et al., "Phenotyping Apathy in Individuals With Alzheimer Disease Using Functional Principal Component Analysis," Am J Geriatr Psychiatry, 2013, 21(4):391-397, 12 pgs.
Zemanick ET, et al., "Inflammation and Airway Microbiota During Cystic Fibrosis Pulmonary Exacerbations," PLoS One, 2013, 8(4):e62917, 13 pgs.
Zhang, X., et al., "CRISPR/Cas9 system: a powerful technology for in vivo and ex vivo gene therapy," Sci. China Life Sci, May 2017, 60(5):468-75, 8 pgs.
Ziady AG, et al., "Interaction with CREB binding protein modulates the activities of Nrf2 and NF-$_{\kappa}$B in cystic fibrosis airway epithelial cells," Am J Physiol Lung Cell Mol Physiol, 2012, 302(11):L1221-L1231, 11 pgs.
Ziady AG, et al., "Protein Sequencing with Tandem Mass Spectrometry," Chapter 21, James Weifu Lee, et al., Eds. *Micro and Nano Technologies in Bioanalysis*, Methods Mol Biol, 2009, 544:325-341, 17 pgs.
Ziady AG, et al., "Proteomic Analyses of BALF Reveal Potential Biomarkers and Suggest Altered Lipid, Cyclic Nucleotide, and Iron Metabolism in Young CF Children Versus Disease Controls," Pediatr Pulmonol, 2013, 48(S36):277-278, 2013 Cystic Fibrosis Conference, Poster Session Abstract 204*, 2 pgs.
Ziady AG, et al., "Proteomic Analyses of Serum From CF Patients With Mild or Severe Disease Reveal the Differential Expression of Proteins That Regulate the Differentiation of Cartilage, Myeloid Leukocytes, and Intestinal Epithelia" Pediatr Pulmonol, 2014, 49(S38):288, 2014 Cystic Fibrosis Conference, Poster Session Abstract 206*, 1 pg.
Ziady, A.G., et al., "Current prospects for gene therapy of cystic fibrosis," Curr Opin Pharmacol, Oct. 2006, 6(5):515-21, 7 pgs.
Ziady, A.G., et al., "Functional evidence of CFTR gene transfer in nasal epithelium of cystic fibrosis mice in Vivo following luminal application of DNA complexes targeted to the serpin-enzyme complex receptor," Mol. Ther., Apr. 2002, 5(4):413-9, 7 pgs.
Ziady, A.G., et al., "Non-viral gene transfer therapy for cystic fibrosis," Expert Opin Biol Ther, Jun. 2003, 3(3):449-58, 10 pgs.
Zwart, N.R., et al., "Graphical Programming Interface: A Development Environment for MR1 Methods.," Magn Reson Med, 2015, 74(5):1449-1460, 12 pgs.
Abedin, S., et al., "Predictive Value of Bronchiolitis Obliterans Syndrome Stage 0p in Chronic Graft-versus-Host Disease of the Lung," Biol Blood Marrow Transplant, 2015, 21(6):1127--1131, 15 pgs.
Amanat, F., et al., "A serological assay to detect SARS-CoV-2 seroconversion in humans," Nat. Med, 2020, 26(7):1033-1036, 16 pgs.
Aurora, P., et al.,"Quality Control for Spirometry in Preschool Children with and without Lung Disease," Am J Respir Crit Care Med, 2004, 169:1152-1159, 8 pgs.
Aziz, M.D., et al., "Disease Risk and GVHD Biomarkers Can Stratify Patients For Risk of Relapse and Non-Relapse Mortality Post Hematopoietic Cell Transplant," Leukemia, 2020, 34(7):1898-1906, 17 pgs.
Benden, C., et al., "Therapy options for chronic lung allograft dysfunction-bronchiliolitis obliterans syndrome following first-line immunosuppressive strategies: A systematic review," Jounral of Heart and Lung Transplantation, 2017, 36(9):921-933, 13 pgs.
Bergeron, A., et al., "Noninfectious lung complications after allogeneic haematopoietic stem cell transplantation," Eur Respir J, 2018, 51:1702617, 13 pgs.
Brewington, J.J., et al., "Detection of CFTR function and modulation in primary human nasal cell spheroids," J Cyst Fibros, 2018, 17(1):26-33, 17 pgs.
Callow, K.A., et al., "The time course of the immune response to experimental coronavirus infection of man," Epidemiol Infect, 1990, 105:435-446, 12 pgs.
Casadevall, A., et al., "The convalescent sera option for containing COVID-19," J Clin Invest, 2020, 130(4):1545-1548.
Centers for Disease Control and Prevention (CDC) Revised U.S. surveillance case definition for severe acute respiratory syndrome (SARS) and update on SARS cases—United States and worldwide, Dec. 2003. MMWR Morb. Mortal. Wkly. Rep., 2003, 52, 1202-1206, 6 pgs.
Chang, C.-K., et al., "Multiple Nucleic Acid Binding Sites and Intrinsic Disorder of Severe Acute Respiratory Syndrome Coronavirus Nucleocapsid Protein: Implications for Ribonucleocapsid Protein Packaging," J Virol, 2009, 83(5):2255-2264, 10 pgs.
Cheng, G.-S., et al., "Lung Function Trajectory in Bronchiolitis Obliterans Syndrome after Allogeneic Hematopoietic Cell Transplant," Ann Am Thorac Soc, 2016; 13(11):1932-1939, 8 pgs.
Chi, X., et al., "A neutralizing human antibody binds to the N-terminal domain of the Spike protein of SARS-CoV-2," Science, 2020, 369:650-655, 6 pgs.
Chien, J.W., et al., "Bronchiolitis Obliterans Syndrome After Allogeneic Hematopoietic Stem Cell Transplantation: An Increasingly Recognized Manifestation of Chronic Graft-versus-Host Disease," Biol Blood Marrow Transplant, 2010, 16(1):S106-S114, 9 pgs.
Cohen, H.Y., et al., "Calorie Restriction Promotes Mammalian Cell Survival by Inducing the SIRT1 Deacetylase," Science, 2004, 305(5682):390-392.

(56) References Cited

OTHER PUBLICATIONS

Cox, D.R., et al., "Large numbers of explanatory variables, a semi-descriptive analysis," PNAS, 2017, 114(32):8592-8595, 4 pgs.
De Silva, T., et al., "Markers of rejection of a lung allograft: state of the art," Biomark Med, 2022, 16(6):483-498, 16 pgs.
Deeks, J.J., et al. "Antibody tests for identification of current and past infection with SARS-CoV-2 (Review)," Cochrane Database Syst Rev, 2020, 6:CD013652, 306 pgs.
Dijkman, R., et al., "Human Coronavirus NL63 and 229E Seroconversion in Children," J Clin Microbiol, 2008, 46(7):2368-2373, 6 pgs.
Du, L., et al., "The spike protein of SARS-CoV—a target for vaccine and therapeutic development," Nat Rev Microbiol, 2009, 7:226--236, 11 pgs.
Dunn, M., et al., "Pediatric Bone Marrow Transplant Recipients That Develop Bronchiolitis Obliterans Syndrome Exhibit Significant Changes in Complement Activation, Angiotensin Maturation, and Cholesterol Processing Prior to Clinical Diagnosis," Am J Respir Crit Care Med, 2021, 203(9):A3281 (Abstract), 2 pgs.
Eroshenko, N., et al., "Implications of antibody-dependent enhancement of infection for SARS-CoV-2 countermeasures," Nat Biotechnol, 2020, 38:789-791, 3 pgs.
Estenne, M., et al., "Bronchiolitis Obliterans Syndrome 2001: An Update of the Diagnostic Criteria," J Heart Lung Transplant, 2002; 21:297-310, 14 pgs.
Fink, Z.W., et al., "PepSIRF: a flexible and comprehensive tool for the analysis of data from highly-multiplexed DNA-barcoded peptide assays," arXiv, 2020, 5 pgs.
Fleri, W., et al., "The Immune Epitope Database and Analysis Resource in Epitope Discovery and Synthetic Vaccine Design," Front Immunol, 2017, 8:278, 16 pgs.
Friesen, R.H.E., et al., "A common solution to group 2 influenza virus neutralization," PNAS, 2014, 111(1):445-450, 6 pgs.
Geyer, P.E., et al., "Plasma Proteome Profiling to Assess Human Health and Disease," Cell Syst, 2016, 2:185-195, 12 pgs.
Geyer, P.E., et al., "Proteomics reveals the effects of sustained weight loss on the human plasma proteome," Mol Syst Biol, 2016; 12:901, 16 pgs.
Gorse, G.J., et al., "Prevalence of Antibodies to Four Human Coronaviruses is Lower in Nasal Secretions than in Serum," Clin Vaccine Immunol, 2010, 17(12):1875-1880, 6 pgs.
Gostic, K.M., et al., "Potent Protection against H5N1 and H7N9 Influenza via Childhood Hemagglutinin Imprinting," Science, 2016, 354(6313):722-726, 16 pgs.
Grassi, N., et al., "Ultra-deep and quantitative saliva proteome reveals dynamics of the oral microbiome," Genome Med, 2016, 8:44, 13 pgs.
Grifoni, A., et al., "Targets of T Cell Responses to SARS-CoV-2 Coronavirus in Humans with COVID-19 Disease and Unexposed Individuals," Cell, 2020, 181:1489-1501, 29 pgs.
Halstead, S.B., et al., "Antibody-enhanced dengue virus infection in primate leukocytes," Nature, 1977, 265:739-741, 3 pgs.
Hansen, J., et al., "Studies in humanized mice and convalescent humans yield a SARS-CoV-2 antibody cocktail," Science, 2020, 369:1010-1014, 5 pgs.
Hartwell, M.J., et al., "An early-biomarker algorithm predicts lethal graft-versus-host disease and survival," JCI Insight, 2017, 2(3):e89798, 9 pgs.
Hassan, J., et al., "Serum $I_gA$ and $IG_g$ Subclasses During Treatment for Acute Respiratory Exacerbation in Cystic Fibrosis: Analysis of Patients Colonised with Mucoid or Non-Mucoid Strains of Pseudomonas Aeruginosa," Immunological Investigations, 1994, 23(1):1-13, 14 pgs.
Heijerman, H.G.M., et al., "Efficacy and safety of the elexacaftor/tezacaftor/ivacaftor combination regimen in people with cystic fibrosis homozygous for the F508del mutation: a double-blind, randomised, phase 3 trial," Lancet, 2019, 394(10212):1940-1948, 21 pgs.
Heltshe, S.L., et al., "Ivacaftor-treated Patients with Cystic Fibrosis Derive Long-Term Benefit Despite No Short-Term Clinical Improvement," Am J Respir Crit Care Med, 2018, 197(11):1483-1486, 4 pgs.
Hildebrandt, G.C., et al., "Diagnosis and treatment of pulmonary chronic GVHD: report from the consensus confrence on clinical practice in chronic GVHD," Bone Marrow Transplant, 2011, 46(10):1283-1295, 13 pgs.
Hoofnagle, J.H., et al., "Antibody to Hepatitis B Core Antigen. A Sensitive Indicator of Hepatitis B Virus Replication," N Engl J Med, 1974, 290:1336-1340, 5 pgs.
Huttenhain, R., et al., "A Targeted Mass Spectrometry Strategy for Developing Proteomic Biomarkers: A Case Study of Epithelial Ovarian Cancer," Mol Cell Proteomics, 2019, 18:1836-1850, 16 pgs.
Jagasia, M.H., et al., "National Institutes of Health Consensus Development Project on Criteria for Clinical Trials in Chronic Graft-versus-Host Disease: I. The 2014 Diagnosis and Staging Working Group Report," Biol Blood Marrow Transplant, 2015, 21(3):389-401.e1, 27 pgs.
Jia, N., et al., "Emergence of human infection with Jingmen tick virus in China: A retrospective study," EBioMedicine, 2019, 43:317-324, 8 pgs.
Jodele, S., et al., "Complement blockade for TA-TMA: lessons learned from a large pediatric cohort treated with eculizumab," Blood, 2020, 135(13):1049-1057, 9 pgs.
Jodele, S., et al., "Interferon-complement loop in transplant-associated thrombotic microangiopathy," Blood Adv, 2020, 4(6):1166-1177, 12 pgs.
Kall, L., et al., "Semi-supervised learning for peptide identification from shotgun proteomics datasets," Nat Methods, 2007, 4(11):923-925, 3 pgs.
Katzelnick, L.C., et al., "Antibody-dependent enhancement of severe dengue disease in humans," Science, 2017, 358:929-932, 4 pgs.
Keng, C.-T., et al., "Amino Acids 1055 to 1192 in the S2 Region of Severe Acute Respiratory Syndrome Coronavirus S Protein Induce Neutralizing Antibodies: Implications for the Development of Vaccines and Antiviral Agents," J Virol, 2005, 79(6):3289-3296, 8 pgs.
Keogh, R.H., et al., "Dynamic Predication of Survival in Cystic Fibrosis: A Landmarking Analysis Using UK Patient Registry Data," Epidemiology, 2019, 30(1):29-37, 9 pgs.
Khan, S., et al., "Analysis of Serologic Cross-Reactivity Between Common Human Coronaviruses and SARS-CoV-2 Using Coronavirus Antigen Microarray," bioRxiv, 2020, 10 pgs.
Khurana, S., et al., "Vaccine-Induced Anti-HA2 Antibodies Promote Virus Fusion and Enhance Influenza Virus Respiratory Disease," Sci Transl Med, 2013, 5(200):200ra114, 10 pgs.
Konstan, M.W., et al., "Risk Factors For Rate of Decline in Forced Expiratory Volume in One Second in Children and Adolescents with Cystic Fibrosis," J Pediatr, 2007, 151(2):134-139e1, 7 pgs.
Konstan, M.W., et al., "Risk Factors For Rate of Decline in $FEV_1$ in Adults with Cystic Fibrosis," J Cyst Fibros, 2012, 11(5):405-411, 15 pgs.
Kozlov, I.A., et al., "A Highly Scalable Peptide-Based Assay System for Proteomics," PLoS One, 2012, 7(6):e37441, 10 pgs.
Krammer, F., et al., "Serology assays to manage COVID-19: Measurement of antibodies to SAR-CoV-2 will improve disease management if used correctly," Science, 2020, 368(6495):1060-1061, 2 pgs.
Krisp, C., et al., "Proteomic phenotyping of metastatic melanoma reveals putative signatures of MEK inhibitor response and prognosis," Br J Cancer, 2018; 119:713-723, 11 pgs.
Ku, N-O., et al., "Mutation of Human Keratin 18 in Association with Cryptogenic Cirrhosis," J Clin Invest, 1997, 99(1):19-23, 5 pgs.
Lai, S.-C., et al., "Characterization of neutralizing monoclonal antibodies recognizing a 15-residues epitope on the spike protein HR2 region of severe acute respiratory syndrome coronavirus (SARS-CoV)," J Biomed Sci, 2005, 12:711-727, 17 pgs.
Larman, H.B., et al. "Application of a synthetic human proteome to autoantigen discovery through PhIP-Seq," Nat Biotechnol, 2011, 29(6):535-541, 19 pgs.
Le, T.T., et al., "The COVID-19 vaccine development landscape," Nat Rev Drug Discov, 2020, 19:305-306, 2 pgs.

(56) References Cited

OTHER PUBLICATIONS

Lederer, D.J., et al., "Control of Confounding and Reporting of Results in Casual Inference Studies: Guidance for Authors form Editors of Respiratory, Sleep, and Critical Care Journals," Ann Am Thorac Soc, 2019, 16(1):22-28, 8 pgs.
Li, D., et al., "Flexible semiparametric joint modeling: an application to estimate individual long function decline and risk of pulmonary exacerbations in cystic fibrosis," Emerg Themes Epidemiol, 2017, 14:13, 13 pgs.
Liu, A., et al., "Antibody responses against SARS-CoV-2 in COVID-19 patients," J Med Virol, 2021, 93:144-148, 5 pgs.
Liu, S., et al., "Interaction between heptad repeat 1 and 2 regions in spike protein of SARS-associated coronavirus: implications for virus fusogenic mechanism and identification of fusion inhibitors," Lancet, 2004, 363:938-947, 10 pgs.
Liu, X., et al., "Proteomic Characterization Revels That MMP-3 Correlates With Bronchiolitits Obliterans Syndrome Following Allogeneic Hematopoietic Cell and Lung Transplantation," Am J Transplant, 2016, 16(8):2342-2351, 28 pgs.
Lounder, D.T., et al., "Lower levels of vitamin A are associated with increased gastrointestinal graft-versus-host disease in children," Blood, 2017, 129(20): 2801-2807, 7 pgs.
Lu, R., et al., "Genomic characterisation and epidemiology of 2019 novel coronavirus: implications for virus origins and receptor binding," Lancet, 2020, 395:565-574, 10 pgs.
Lubroth, J., et al., "Absence of protein 2C from clarified foot-and-mouth disease virus vaccines provides the basis for distinguishing convalescent from vaccinated animals," Vaccine, 1996, 14(5):419-427, 9 pgs.
Lucchese, G., et al., "Peptidology: short amino acid modules in cell biology and immunology," Amino Acids, 2007, 33:703-707, 5 pgs.
Luebbering, N., et al., "Endothelial injury, F-actin and vitamin D binding protein after hematopoietic stem cell transplant and association with clinical outcomes," Haematologica, 2021, 106(5):1321-1329, 9 pgs.
Lv, H., et al., "Cross-reactive Antibody Response between SARS-CoV-2 and SARS-CoV Infections," Cell Rep, 2020, 31:107725, 10 pgs.
Magi, B. et al., "Bronchoalveolar lavage fluid protein composition in patients with sarcoidosis and idiopathic pulmonary fibrosis: A two-dimensional electrophoretic study," Electrophoresis, 2002, 23:3434-3444, 11 pgs.
Major-Monfried, H., et al., "MAGIC biomarkers predict long-term outcomes for steroid-resistant acute GVHD," Blood, 2018, 131(25):2846-2855, 10 pgs.
Middleton, P.G., et al., "Elexacaftor-Tezacaftor-Ivacaftor for Cystic Fibrosis with a Single Phe508del Allele," N Engl J Med, 2019, 381(19):1809-1819, 16 pgs.
Mina, M.J., et al., "Measles virus infection diminishes preexisting antibodies that offer protection from other pathogens," Science, 2019, 366(6465):599-606, 18 pgs.
Monto, A.S., et al., "The Doctrine of Original Antigenic Sin: Separating Good From Evil," J Infect Dis, 2017, 215:1782-1788, 7 pgs.
Muhlebach, M.S, et al., "Biomarkers for Cystic Fibrosis Drug Development," J Cyst Fibros, 2016, 15(6):714-723, 20 pgs.
Ni, L., et al., "Detection of SARS-CoV-2-Specific Humoral and Cellular Immunity in COVID-19 Convalescent Individuals," Immunity, 2020, 52:971-977, 11 pgs.
Nichols, D.P., et al., "The triterpenoid CDDO limits inflammation in preclinical models of cystic fibrosis lung disease," Am J Physiol Lung Cell Mol Physiol, 2009, 297(5):L828-L836, 9 pgs.
Nie, J., et al., "Establishment and validation of a pseudovirus neutralization assay for SARS-CoV-2," Emerg Microbes Infect, 2020, 9:680-686, 7 pgs.
Pillay, T.S., "Gene of the month: the 2019-nCoV/SARS-CoV-2 novel coronavirus spike protein," J Clin Pathol, 2020, 73:366-369, 4 pgs.
Pinto, D., et al., "Cross-neutralization of SARS-CoV-2 by a human monoclonal SARS-CoV antibody," Nature, 2020, 583:290-295, 22 pgs.
Poh, C.M., et al., "Two linear epitopes on the SARS-CoV-2 spike protein that elicit neutralising antibodies in COVID-19 patients," Nat Commun, 2020, 11:2806, 7 pgs.
Price, J.V., et al., "'On silico' peptide microarrays for high-resolution mapping of antibody epitopes and diverse protein-protein interactions," Nat Med, 2012, 18(9):14341440, 16 pgs.
The R Core Team, "R: A Language and Environment for Statistical Computing, R Version 3.5.2" Vienna, Austria, R Foundation for Statistical Computing, 2018, https://www/R-project.org/, 3636 pgs.
Robbiani, D.F., et al., "Convergent Antibody Responses to SARS-CoV-2 in Convalescent Individuals," Nature, 2020, 584(7821):437-442, 35 pgs.
Routledge, E., et al., "Analysis of Murine Coronavirus Surface Glycoprotein Functions by Using Monoclonal Antibodies," J Virol, 1991, 65(1):254-262, 9 pgs.
Rowe, S.M., et al., "Clinical Mechanism of the Cystic Fibrosis Transmembrane Conductance Regulator Potentiator Ivacaftor in G551D-mediated Cystic Fibrosis," Am J Respir Crit Care Med, 2014, 190(2):175-184, 10 pgs.
Rubin, D.B., "Inference and Missing Data," Biometrika, 1976, 63(3):581-592, 12 pgs.
Schaad, U.B., et al., "Serotype-Specific Serum $I_g$G Antibodies to Lipopolysaccharides of *Pseudomonas aeruginosa* in Cystic Fibrosis: Correlation to Disease, Subclass Distribution, and Experimental Protective Capacity," Pediatric Research, 1990, 27(5):508-513, 6 pgs.
Schluchter, M.D., et al., "Jointly modelling the relationship between survival and pulmonary function in cystic fibrosis patients," Stat Med, 2002, 21:1271-1287, 17 pgs.
Shiryaev, S.A., et al., "New Details of HCV NS3/4A Proteinase Functionality Revealed by a High-Throughput Cleavage Assay," PLoS One, 2012, 7(4):e35759, 12 pgs.
Soares, H.D., et al., "Biomarkers Associated With the Apolipoprotein E Genotype and Alzheimer Disease," Arch Neurol, 2012, 69(10):1310-1317, 16 pgs.
Spivak, M., et al., "Improvements to the Percolator algorithm for peptide identification from shotgun proteomics data sets," J Proteome Res, 2009, 8(7):3737-3745, 22 pgs.
Srinagesh, H.K., et al., "The MAGIC algorithm probability is a validated response biomarker of treatment of acute graft-versus-host disease," Blood Advances, 2019, 3(23):4034-4042, 9 pgs.
Su, W., et al., "An empirical comparison of segmented and stochastic linear mixed effects models to estimate rapid disease progression in longitudinal biomarker studies," Stat Biopharm Res, 2021, 13(3):270-279, 22 pgs.
Tamburro, R.F., et al., "Pulmonary Complications of Pediatric Hematopoietic Cell Transplantation: A National Institutes of Health Workshop Summary," Ann Am Thorac Soc, 2021, 18(3):381-394, 14 pgs.
Tan, C.W., et al., "A SARS-CoV-2 surrogate virus neutralization test based on antibody-mediated blockage of ACE2-spike protein-protein interaction," Nat Biotech, 2020, 38:1073-1078, 17 pgs.
Tissot, A., et al., "Early Identification of Chronic Lung Allograft Dysfunction: The Need of Biomarkers," Frontiers in Immunology, 2019, 10:Article 1681, 13 pgs.
Uhl Ving, H.H., et al., "Bronchiolitis obliterans after allo-SCT: clinical criteria and treatment options," Bone Marrow Transplantation, 2012, 47:1020-1029, 10 pgs.
Van Der Ploeg, E.A., et al., "The potenial of biomarkers of fibrosis in chronic lung allograft dysfunction," Transplantation Reviews, 2021, 35(3):100626, 11 pgs.
Veraar, C., et al., "Potential novel biomarkers for chronic lung allograft dysfunction and azithromycin responsive allograft dysfunction," Scientific Reports, 2021, 11(1):6799, 13 pgs.
Verhaeghe, C., et al., "Intrinsic pro-angiogenic status of cystic fibrosis airway epithelial cells," BioChemical and Biophysical Research Communications, 2007, 356:745-749, 5 pgs.
Verleden, G.M., et al., "Azithromycin Reduces Airway Neutrophilia and Interleukin-8 in Patients with Brochiolitis Obliterans Syndrome," Am J Respir Crit Care Med, 2006, 174:556-570, 5 pgs.

(56) References Cited

OTHER PUBLICATIONS

Verleden, S.E., et al., "Chronic lung allograft dysfunction phenotypes and treatment," Journal of Thoracic Disease, 2017, 9(8):2650-2659, 11 pgs.
Volkova, N., et al., "Disease progression in patients with cystic fibrosis treated with ivacaftor: Data from national US and UK registries," J Cystic Fibros, 2020, 19:68-79, 12 pgs.
Walls, A.C., et al., "Tectonic conformational changes of a coronavirus spike glycoprotein promote membrane fusion," PNAS, 2017, 114(42):11157-11162, 6 pgs.
Waterhouse, A., et al., "Swiss-Model: homology modelling of protein structures and complexes," Nucleic Acids Res, 2018, 46:W296-W303, 8 pgs.
Wewer Albrechtsen, N.J., et al., "Plasma Proteome Profiling Reveals Dynamics of Inflammatory and Lipid Homeostasis Markers after Roux-En-Y Gastric Bypass Surgery," Cell Syst, 2018, 7:601-612. e1-e3, 16 pgs.
Whitman, J.D., et al., "Test performance evaluation of SARS-CoV-2 serological assays," Nat Biotechnol, 2020, 38(10):1174-1183, 26 pgs.
Wolff, D., et al., "Biomarkers in chronic graft-versus-host disease—quo vadis?" Bone Marrow Transplant, 2018, 53(7):832-837, 10 pgs.
Woolhouse, M.E.J., et al., "Epidemiological characteristics of human-infective RNA viruses," Sci Data, 2018, 5:180017, 6 pgs.
Xia, S., et al., "A pan-coronavirus fusion inhibitor targeting the HR1 domain of human coronavirus spike," Sci Adv, 2019, 5:eaav4580, 15 pgs.
Xu, G.J., et al., "Comprehensive serological profiling of human populations using a synthetic human virome," Science, 2015, 348(6239):aaa0698, 23 pgs.
Yu, J., et al., "Biomarker Panel for Chronic Graft-Versus-Host Disease," J Clin Oncol, 2016, 34(22): 2583-2590, 10 pgs.
Yuan, M., et al., "A highly conserved cryptic epitope in the receptor-binding domains of SARS-CoV-2 and SARS-CoV," Science, 2020, 368:630-633, 4 pgs.
Zhu, N., et al., "A Novel Coronavirus from Patients with Pneumonia in China, 2019," N Engl J Med, 2020, 382(8):727-733, 7 pgs.
Ziady, A.G., et al., "Redox balance in cystic fibrosis," Int J Biochem Cell Biol, 2014, 0:113-123, 27 pgs.
Zost, S.J., et al., "Potently neutralizing and protective human antibodies against SARS-CoV-2," Nature, 2020, 584(7821):443-449, 34 pgs.

* cited by examiner

COMPOSITIONS COMPRISING A TWEAK LIGAND AND METHODS OF USING SAME

CROSS-REFERENCE TO RELATED APPLICATIONS

This application claims priority to and benefit of International Application No. PCT/US20/30401 entitled "Compositions Comprising a Tweak Ligand and Methods of Using Same," filed Apr. 29, 2020, which claims priority to and benefit of U.S. Provisional Application No. 62/839,970, filed Apr. 29, 2019, to Ziady, the contents of which are incorporated in their entirety for all purposes.

STATEMENT REGARDING FEDERALLY-SPONSORED RESEARCH

This invention was made with government support under EB023800 awarded by The National Institutes of Health. The government has certain rights in the invention.

BACKGROUND

Brain cancer is the leading cause of cancer-related death in patients younger than 35 years of age. The most common and deadly primary brain tumor is glioblastoma (GBM), which accounts for approximately 40% of primary brain tumors, is the most malignant form of astrocytoma and is synonymous with a grade IV glioma. Surgery alone cannot cure GBM because highly invasive tumor cells infiltrate the surrounding brain, making surgical removal without catastrophic damage to healthy brain tissue nearly impossible. Glioblastoma is the most common and aggressive type of primary brain tumor and is characterized by extensive angiogenesis and tumor cell infiltration deep into the normal brain parenchyma[1]. Despite aggressive rounds of chemotherapy and/or radiation followed by surgical resection, the patients' quality of life is very poor with a median survival of 20 months[2], necessitating an advanced therapeutic option. Painstaking genetic association studies have recently revealed various powerful genetic targets that confer a potential to stop or even reverse tumor progression[3]. This, in conjunction with innovations in gene delivery technology, has resurfaced hope for more effective GBM therapies, and has spawned numerous Phase I clinical trials evaluating post-surgery delivery of therapeutic genes via novel gene delivery systems (i.e. vectors)[4]. However, later stage clinical trials have failed to demonstrate efficient gene transfer enough to mediate significant improvement in therapeutic outcomes, due largely to numerous delivery barriers and ubiquitous therapeutic transgene expression[4,5].

BRIEF SUMMARY

The instant disclosure relates to nanoparticle compositions that may be used for the targeting of certain cells or tissues. The nanoparticles may take a variety of different forms, including non-viral, viral, and lipid nanoparticles, and may utilize a TNF receptor superfamily member 12A ("TWEAKR") binding region of the TWEAK protein to target a nanoparticle to tissues expressing TWEAKR. The compositions may further comprise a suicide gene optionally under the control of a tissue specific promoter. In further aspects, methods of treating an individual using the disclosed nanoparticle compositions are described.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION

Definitions

Figure 1:
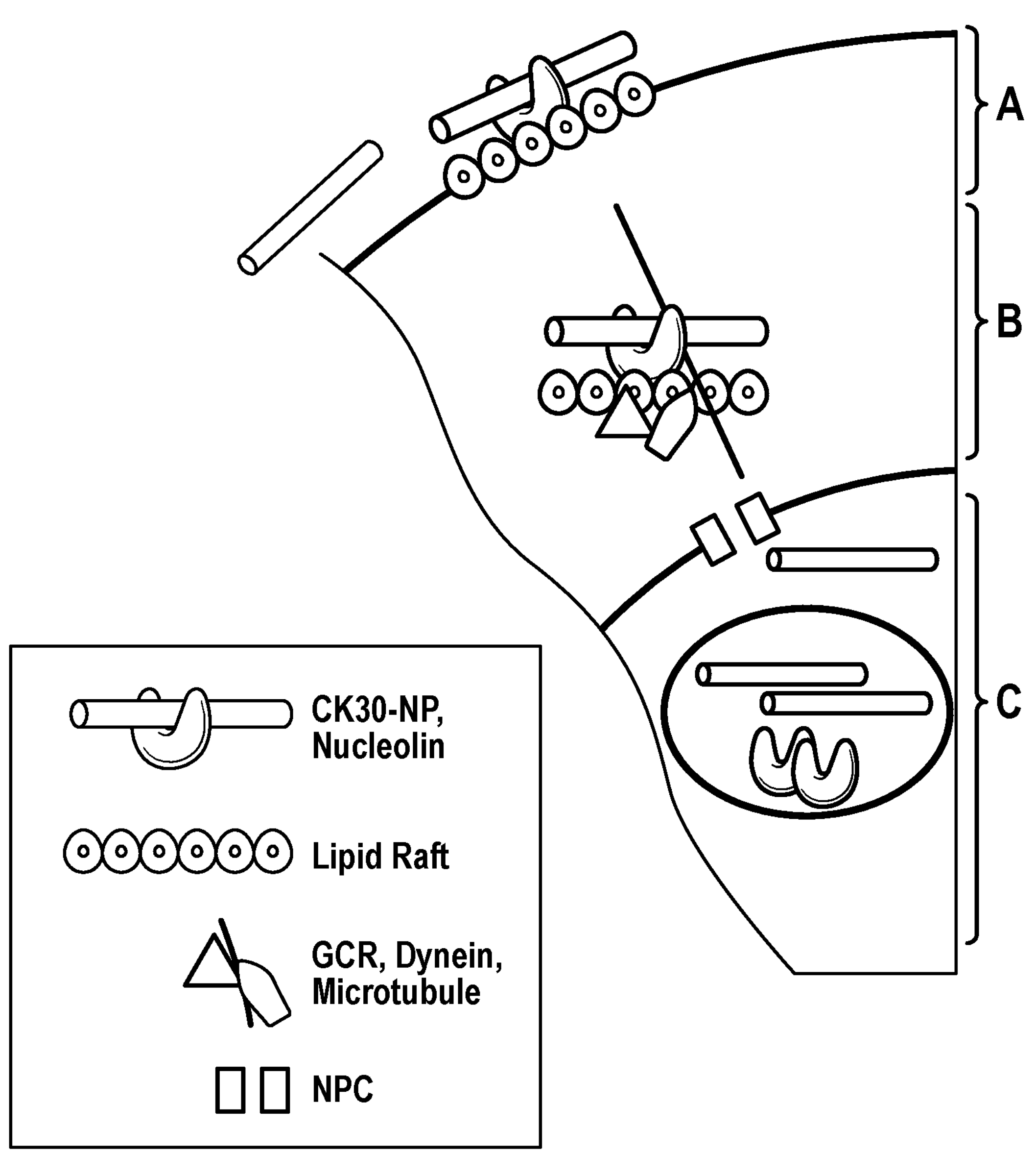
FIG. 1. Diagram of CK30PEG nanoparticle (NP) trafficking. (A) First trafficking steps involve CK30PEG DNP binding to a cognate receptor such as nucleolin for NPs. (B) CK30PEG NPs are internalized via raft-mediated endocytosis and traffic to the nucleus, using the cellular microtubule system. (C) The mechanisms for CK30PEG NP entry in the nucleus are not clear but may rely on diffusion through the nuclear pore complex (NPC) or processing by nuclear receptors. Diagram is a modification of a figure from Invest. Ophthalmol. Vis. Sci., 52(6): 3051.

Unless otherwise noted, terms are to be understood according to conventional usage by those of ordinary skill in the relevant art. In case of conflict, the present document, including definitions, will control. Preferred methods and materials are described below, although methods and materials similar or equivalent to those described herein may be used in practice or testing of the present invention. All publications, patent applications, patents and other references mentioned herein are incorporated by reference in their entirety. The materials, methods, and examples disclosed herein are illustrative only and not intended to be limiting.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" may mean within 1 or more than 1 standard deviation, per the practice in the art. Alternatively, "about" may mean a range of up to 20%, or up to 10%, or up to 5%, or up to 1% of a given value. Alternatively, particularly with respect to biological systems or processes, the term may mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "effective amount" means the amount of one or more active components that is sufficient to show a desired effect. This includes both therapeutic and prophylactic effects. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms may refer to children.

"Sequence identity" as used herein indicates a nucleic acid sequence that has the same nucleic acid sequence as a reference sequence, or has a specified percentage of nucleotides that are the same at the corresponding location within a reference sequence when the two sequences are optimally aligned. For example a nucleic acid sequence may have at least 50%, 60%, 70%, 75%, 80%, 85%, 90%, 95%, 96%, 97%, 98%, 99%, or 100% identity to the reference nucleic acid sequence. The length of comparison sequences will generally be at least 5 contiguous nucleotides, preferably at least 10, 11, 12, 13, 14, 15, 16, 17, 18, 19, 20, 21, 22, 23, 24, or 25 contiguous nucleotides, and most preferably the full length nucleotide sequence. Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

The term "NNP" refers to a Nucleic acid Nano Particle. A non-limiting example includes a complex of DNA or RNA with polymers of lysines (for example, 15-45 lysines long)

The term "DNP" refers to a DNA Nanoparticle

The term "RNP" refers to a RNA Nanoparticle

Disclosed herein are methods and compositions that address one or more of the aforementioned needs in the art.

In one aspect, a method of treating a tumor, particularly a brain tumor, more particularly glioblastoma (GBM), is disclosed. In one aspect, the method may comprise the step of administering to an individual in need thereof a composition comprising a nanoparticle that is conjugated to a protein or peptide ligand comprising at least a portion of the ligand for TNF receptor superfamily member 12A ("TWEAKR").

TWEAK protein is a cytokine that belongs to the tumor necrosis factor (TNF) ligand family. This protein is a ligand for the FN14/TWEAKR receptor. This cytokine has overlapping signaling functions with TNF, but displays a much wider tissue distribution. This cytokine, which exists in both membrane-bound and secreted forms, can induce apoptosis via multiple pathways of cell death in a cell type-specific manner. This cytokine is also found to promote proliferation and migration of endothelial cells, and thus acts as a regulator of angiogenesis. Alternative splicing results in multiple transcript variants. Some transcripts skip the last exon of this gene and continue into the second exon of the neighboring TNFSF13 gene; such read-through transcripts are contained in GeneID 407977, TNFSF12-TNFSF13. In certain aspects, for example, suitable peptides or proteins that bind to TWEAKR may have at least 50%, 60%, 70%, 75%, 80%, 85%, 90%, 95%, 96%, 97%, 98%, 99%, or 100% identity to a ligand for TWEAKR, provided the peptide and/or protein binds, to some extent, to TWEAKR. TWEAKR is described in, for example, Hersh D S, Harder B G, Roos A, Peng S, Heath J E, Legesse T, Kim A J, Woodworth G F, Tran N L, Winkles J A. The TNF receptor family member Fn14 is highly expressed in recurrent glioblastoma and in GBM patient-derived xenografts with acquired temozolomide resistance. Neuro Oncol. 2018 Sep. 3; 20(10):1321-1330. doi: 10.1093/neuonc/noy063. PMID: 29897522; PMCID: PMC6140775. In one aspect, the protein or peptide comprises a TWEAK moiety having at least 90% homology to a portion of the TNF superfamily member 12 (TWEAK) protein. It will be readily understood to one of ordinary skill in the art that a suitable peptide and/or protein for use with the disclosed compositions and methods may be one that has less than 100% sequence homology to that of a wild-type TWEAKR ligand, in particular, the TNF superfamily member 12 (TWEAK) protein. It is contemplated that the peptide and/or protein useful for the claimed invention may include the use of any portion of the TWEAK protein capable of binding TWEAKR, and is not limited to full length TWEAK or inclusion of non-binding regions of TWEAK. The TWEAK moiety may comprise less than 90% or less than 80% or less than 70% or less than 60% or less than 50% or less than 40% or less than 30% or less than 20% or less than 10% of the full-length TWEAK protein.

In one aspect, the nanoparticle of the disclosed compositions and methods may comprise at least one TWEAK moiety, or at least two TWEAK moieties, or at least three TWEAK moieties, or at least four TWEAK moieties, or at least five TWEAK moieties, or at least six TWEAK moieties, or at least seven TWEAK moieties, or at least eight TWEAK moieties, or at least nine TWEAK moieties, or at least ten TWEAK moieties, or greater than at least 10 tweak moieties per nanoparticle. In further aspects, the compositions may comprise a mixture of nanoparticles having various degrees of TWEAK moiety substitution.

The nanoparticle may take a variety of different forms, and may include viral vectors or lipid nanoparticles. For example, in certain aspects, the nanoparticle may be selected from one or more of a nucleic acid nanoparticle, a DNA nanoparticle, an RNA nanoparticle, a viral nanoparticle, a lipid nanoparticle, or combinations thereof.

In one aspect, the nanoparticle may comprise a DNA plasmid encoding for a gene, wherein expression of the gene is desired. In one aspect, the gene may be a suicide gene. Such genes are readily understood by one of ordinary skill in the art. The term "suicide gene" includes any gene that expresses a product that is fatal to the cell expressing the suicide gene. Suitable, nonlimiting suicide genes include, for example, Caspase 9 (or caspase 3 or 7, upon which AP1903 may be administered to activate the suicide gene); thymidine kinase (TK) (upon which ganciclovir (GCV) may be administered to activate the suicide gene); cytosine deaminase (CD) (upon which 5-fluorocytosine (5-FC) can be administered to activate the suicide gene), and combinations thereof. A representative example of such a suicide gene is one which codes for thymidine kinase of herpes simplex virus. Additional examples are thymidine kinase of varicella zoster virus and the bacterial gene cytosine deaminase which can convert 5-fluorocytosine to the highly toxic compound 5-fluorouracil. Suicide genes also include as non limiting examples caspase-9 or caspase-8 or cytosine deaminase. Caspase-9 can be activated using a specific chemical inducer of dimerization (CID). Suicide genes can also be polypeptides that are expressed at the surface of the cell and can make the cells sensitive to therapeutic monoclonal antibodies. As used herein "prodrug" means any compound useful in the methods of the present invention that can be converted to a toxic product. The prodrug is converted to a toxic product by the gene product of the suicide gene in the method of the present invention. A representative example of such a prodrug is ganciclovir which is converted in vivo to a toxic compound by HSV-thymidine kinase. The ganciclovir derivative subsequently is toxic to tumor cells. Other representative examples of prodrugs include acyclovir, FIAU [1-(2-deoxy-2-fluoro-β-D-arabinofuranosyl)-5-iodouracil], 6-methoxypurine arabinoside for VZV-TK, and 5-fluorocytosine for cytosine deaminase. In one aspect, the gene may be under the transcriptional control of a promoter, for example a glioma-cell specific promoter. For example, the promoter may be selected from survivin, hTERT, PEG-3, nestin, or combinations thereof.

In one aspect, the nanoparticle may comprise a PEGylated lysine polymer having a length of from about 12 to about 60 or about 24 to about 40, or about 30 lysine residues. The nanoparticle may comprise a lysine polymer, wherein said lysine polymer further comprises at least one cysteine residue. In a yet further aspect, the nanoparticle may comprise a PEG-CK30 polymer. In one aspect, the nanoparticle may be a 5 k pegylated nanoparticle (see, e.g. references 48-52).

The methods may include nanoparticles having a variety of different shapes. For example, the nanoparticle may have a shape selected from rod, spheroid, or toroid like.

The method may employ a variety of different carriers to administer the compositions. In one exemplary aspect, the nanoparticle may be delivered in a hypertonic solution, for example, a hypertonic saline solution. In one aspect, the hypertonic solution may be one which is about 3% saline. The hypertonic solution may be one sufficient to expand space in the extracellular matrix, thus allowing for a wider distribution of nanoparticles.

In one aspect, the administering step may be carried out via intravenous injection, intraperitoneal injection, intracranial, and/or intracerebral injection. The injection may be directly into the site of tumor cells, in particular, into a brain tumor cell via intracranial injection. In one aspect, the injection may be carried out using convection enhanced delivery (CED) such as that described in, for example, Debinski, Waldemar, and Stephen B Tatter. "Convection-enhanced delivery for the treatment of brain tumors." Expert review of neurotherapeutics vol. 9,10 (2009): 1519-27. doi:10.1586/ern.09.99. CED may be used to bypass the BBB by directly delivering the therapeutic to a brain tumor. The volume of administration may be from about 10 to about 20 uL in volume, and may be repeated at an interval. For example, the treatment may be repeated monthly, every three weeks, every two weeks, weekly, every three days, every two days, daily, or twice a day or more. In a further aspect, the individual being treated may be treated with irradiation before, during, or after administration of the described nanoparticles, or any combination of such sequence.

Also disclosed are compositions that may comprise a nucleic acid nanoparticle having a first component comprising a CpG-depleted plasmid and a second component comprising a protein or peptide that binds to TWEAKR as described herein. For example, the second component may be a TWEAK moiety having at least 90% homology to a TNF superfamily member 12 (TWEAK) protein as described herein. The nucleic acid nanoparticle may further comprise a suicide gene as described herein. The nanoparticle may comprise a plasmid comprising the suicide gene, which may further be under the control of a promoter, for example a glioma-specific promoter such as survivin, hTERT, PEG-3 or nestin. The compositions may comprise a nanoparticle comprising a polyethylene glycol-substituted poly-L-lysine (PEGylated lysine polymer), wherein said lysine polymer comprises at least one cysteine residue, for example, a PEGylated lysine polymer having a length of from about 12 to about 60 or about 24 to about 40, or about 30 lysine residues. The lysine polymer may comprise at least one cysteine residue. In one aspect, the polymer may be PEG-CK30. The nanoparticle may take a variety of different shapes, for example the nanoparticle may have a shape selected from rod, spheroid, or toroid like shape.

Nanoparticle Counterions

The disclosed nanoparticles may contain nucleic acids such as DNA or RNA, which may be double or single stranded, and which may be protein coding or anti-sense coding or non-coding. The nucleic acids may include analogs of RNA and/or DNA (including, for example, miRNA, shRNA, tRNA, siRNA, single and double stranded DNA) that are modified to enhance degradation in vivo. In certain aspects, the nucleic acids are DNA plasmids.

General methods of making nanoparticles are known in the art. See, for example U.S. Pat. No. 8,017,577, entitled "Lyophilizable and enhanced compacted nucleic acids," and/or "Chapter 33: Real-Time Imaging of Gene Delivery and Expression with DNA Nanoparticle Technologies" by Sun and Ziady, filed herewith, both of which are incorporated herein in their entirety by reference. Disclosed herein are alternate counterions to those disclosed in the art which are used to manufacture nucleic acid nanoparticles. Counterions of polycations used to compact nucleic acids are known to affect the shape of particles formed. Shape may be associated with nuclease resistance and colloidal stability. Moreover, shape may affect the suitability and efficacy of compacted nucleic acid complexes for transfecting cells by various routes into a mammalian body.

Counterions used in making compacted nucleic acid complexes may also have an effect on the stability of the complexes to lyophilization. The disclosed nanoparticles may use, for example, non-limiting counterions that may be used include one or more counterions selected from acetate, trifluoroacetate (TFA), bromide, bicarbonate, glutamate, aspartate, hydroxyl ions, or combinations thereof, which may be used before compaction of the nucleic acid.

Exemplary polycations are set forth above and may include polyamino acids such as polylysine and derivatives of polylysine. The polycation may contain from 15-60 lysine residues, preferably in the ranges of 15-30, 30-45, or 45-60 residues. Exemplary derivatives of polylysine are CK15, CK30, CK45, which have an additional cysteine residue attached to polylysine polymers of length 15, 30, and 45 residues, respectively. Other amino acids can be readily attached to polylysine. Other polycationic amino acid polymers can be used such as polyarginine, or copolymers of arginine and lysine. Polymers of non-protein amino acids, such as ornithine or citrulline, could also be used. Any pharmaceutically approved or appropriate polycation can be used including but not limited to protamine, histones, polycationic lipids, putrescine, spermidine, spermine, peptides, and polypeptides. The polycation may also contain a targeting moiety, which is typically a ligand which binds to a receptor on a particular type of cell. The targeting ligand may be a polyamino acid or other chemical moiety. Specificity of interaction of the ligand and the receptor is important for purposes of targeting. In one aspect, the polycation may be reacted with a bifunctional PEG (e.g. maleimide or OPSS to allow for the addition of a targeting moiety.

Pharmaceutical Compositions

In general, the compositions provided herein may be administered in a dosage form. Administration may take a variety of routes, and may include, for example, intracranial, intravenous, or subcutaneous administration, which may include administration of a unit dosage form.

The pharmaceutical compositions may be, in some aspects, isotonic with the blood or other body fluid of the recipient. The isotonicity of the compositions may be attained using sodium tartrate, propylene glycol or other inorganic or organic solutes. An example includes sodium chloride. Buffering agents may be employed, such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. In other aspects, hypertonic solutions of any of the foregoing may be advantageous and are within the scope of the invention.

A pharmaceutically acceptable preservative may be employed to increase the shelf life of the pharmaceutical compositions. Benzyl alcohol may be suitable, although a variety of preservatives including, for example, parabens, thimerosal, chlorobutanol, or benzalkonium chloride may also be employed. A suitable concentration of the preservative is typically from about 0.02% to about 2% based on the total weight of the composition, although larger or smaller amounts may be desirable depending upon the agent selected. Reducing agents, as described above, may be advantageously used to maintain good shelf life of the formulation.

In one aspect, active agents provided herein may be in admixture with a suitable carrier, diluent, or excipient such as sterile water, physiological saline, glucose, or the like, and may contain auxiliary substances such as wetting or emulsifying agents, pH buffering agents, gelling or viscosity enhancing additives, preservatives, and the like, depending upon the route of administration and the preparation desired.

A dosage appropriate to the patient and the number of doses to be administered daily may thus be conveniently selected. In certain embodiments two or more of the therapeutic agents may be incorporated to be administered into a single dosage form (e.g., in a combination therapy); however, in other embodiments the therapeutic agents may be provided in separate dosage forms.

In some embodiments, an active agent provided herein may be administered by intravenous, parenteral, or other injection, in the form of a pyrogen-free, parenterally acceptable aqueous solution or oleaginous suspension. Suspensions may be formulated according to methods well known in the art using suitable dispersing or wetting agents and suspending agents. The preparation of acceptable aqueous solutions with suitable pH, isotonicity, stability, and the like, is within the skill in the art. In some embodiments, a pharmaceutical composition for injection may include an isotonic vehicle such as 1,3-butanediol, water, isotonic sodium chloride solution, Ringer's solution, dextrose solution, dextrose and sodium chloride solution, lactated Ringer's solution, or other vehicles as are known in the art. In addition, sterile fixed oils may be employed conventionally as a solvent or suspending medium. For this purpose, any bland fixed oil may be employed including synthetic mono or diglycerides. In addition, fatty acids such as oleic acid may likewise be used in the formation of injectable preparations. The pharmaceutical compositions may also contain stabilizers, preservatives, buffers, antioxidants, or other additives known to those of skill in the art.

The duration of the injection may be adjusted depending upon various factors, and may comprise a single injection administered over the course of a few seconds or less, to 0.5, 0.1, 0.25, 0.5, 0.75, 1, 2, 3, 4, 5, 6, 7, 8, 9, 10, 11, 12, 13, 14, 15, 16, 17, 18, 19, 20, 21, 22, 23, or 24 hours or more of continuous administration.

In some embodiments, the active agents provided herein may be provided to an administering physician or other health care professional in the form of a kit. The kit is a package which houses a container which contains the active agent(s) in a suitable pharmaceutical composition, and instructions for administering the pharmaceutical composition to a subject. The kit may optionally also contain one or more additional therapeutic agents currently employed for treating a disease state as described herein. For example, a kit containing one or more compositions comprising active agents provided herein in combination with one or more additional active agents may be provided, or separate pharmaceutical compositions containing an active agent as provided herein and additional therapeutic agents may be provided. The kit may also contain separate doses of a active agent provided herein for serial or sequential administration. The kit may optionally contain one or more diagnostic tools and instructions for use. The kit may contain suitable delivery devices, e.g., syringes, and the like, along with instructions for administering the active agent(s) and any other therapeutic agent. The kit may optionally contain instructions for storage, reconstitution (if applicable), and administration of any or all therapeutic agents included. The kits may include a plurality of containers reflecting the number of administrations to be given to a subject.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus may be considered to constitute examples of modes for its practice. However, those of skill in the art should, in light of the present disclosure, appreciate that many changes may be made in the specific embodiments that are disclosed and still obtain a like or similar result without departing from the spirit and scope of the invention.

Example 1

Applicant has investigated the feasibility of using non-viral, synthetic nanoparticles as therapeutic vehicles to insert genes into brain cells. The effect of these therapeutic nanoparticles has been studied by Applicant in an animal model of neurodegeneration[6]. Compacted DNA nanoparticles (DNP) may have, in one aspect, one molecule of plasmid DNA and a 30-mer lysine polymer substituted with polyethylene glycol ($CK_{30}$PEG10k). These DNP may be used to transfect both neurons and astrocytes when injected into brain[7], and can induce sustained transgene expression in brain for greater than one year[8]. Applicant has demonstrated, using an astrocyte-specific promoter, that transgene expression may be directly correlated to age-related and/or lesion-induced changes in the number of astrocytes[9]. Cell surface nucleolin is one mechanism that may be responsible for transporting DNP into cells. It has been reported that cell surface nucleolin serves as a receptor for DNP and that nucleolin is essential for internalization and/or transport of the nanoparticles from cell surface to the nucleus[10] (FIG. 1). As nucleolin is highly over-expressed in tumors[11] and gliomas[12, 13], brain tumors over-expressing nucleolin may be more likely to take up DNP than the surrounding normal brain tissue.

In order to more specifically target tumor cells, Applicant identified a cellular marker that could be used to distinguish tumorigenic cells from normal brain cells. One candidate that stood out among others was the Fn14 receptor, which is also known as TWEAKR or TNFRSF12A. Fn14 is a highly inducible cell-surface receptor that is linked to several intracellular signaling pathways, including the nuclear factor-i4 (NF-i4) pathway[14]. The natural ligand for Fn14, TWEAK, binds with an interaction affinity constant (Kd) of ~0.8-2.4 nM (high affinity) and is the only TNF superfamily member that binds to this receptor[15]. TWEAK is a 14 kDa protein that can be conjugated to a DNP without significantly increasing the nanoparticle size. Fn14 is minimally expressed in normal brain while most GBM tumors are Fn14+ (~80%)[14, 16-19] Fn14 is highly overexpressed on invasive glioma cells[14, 19-22]. Fn14 undergoes constitutive receptor internalization[23], which may be useful in facilitating therapeutic agent delivery[14].

Figure 3:
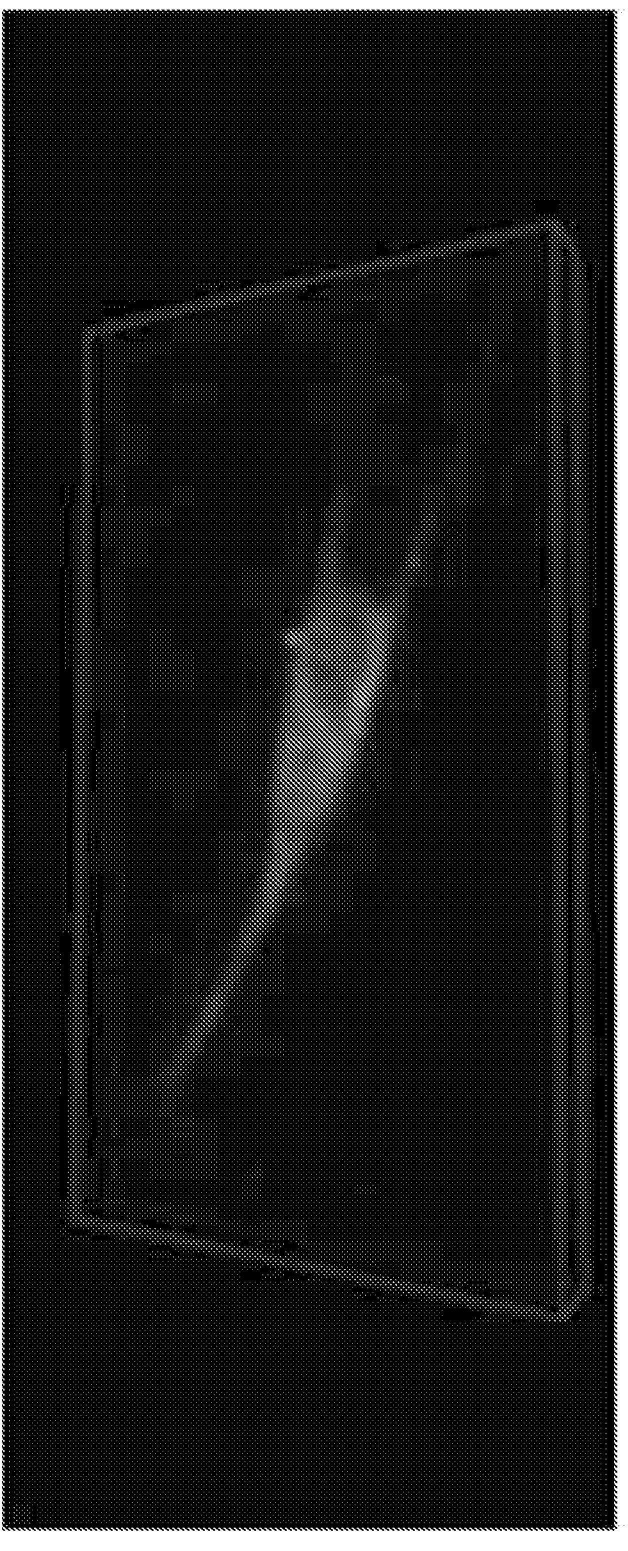
FIG. 3. Confocal image of a U87 cell immunolabelled for Fn14. Red=Fn14, blue=cell nucleus (DAPI).

Applicant has shown that the U87 glioma cell line highly overexpresses Fn14 on the cell surface (FIG. 3). A recent study demonstrated that a Fn14-targeted construct containing a TWEAK moiety was highly internalized by Fn14-overexpressing cells[24]. Moreover, it was recently speculated that Fn14 levels may increase following brain irradiation, which could in theory sensitize radioresistant GB cells to Fn14-targeted therapeutics[25]. By conjugating the TWEAK moiety to DNP, uptake of DNP into tumor cells may be achieved by utilizing two different receptor/uptake mechanisms (nucleolin/Fn14) that are highly upregulated relative to their expression on normal brain cells.

Another means to further reduce off-target effects of therapeutic DNP is to compact plasmid DNA in which the therapeutic transgene is under transcriptional control of a target-specific promoter. By restricting transgene expression to only the targeted cells, in this case tumor cells, transgene expression in off-target, normal brain cells can be reduced. For instance, Applicant has demonstrated that, when DNP is injected intracerebrally, transgene expression can be specifically restricted to astrocytes by encoding the plasmid with a promoter that is activated by a protein, glial fibrillary acidic protein (GFAP), which is highly expressed in astrocytes and negligibly expressed in neurons[9]. Likewise, promoters that drive transgene expression with tumor-specificity can be used. These may include, for example, glioma/tumor-specific promoters such as survivin[26, 27], hTERT[28], PEG-3[29, 30] and nestin[31]. By using target specificity, DNPs may be used as vehicles to transfect tumor cells with a “suicide gene”. Our DNP will contain plasmid DNA encoding for cytosine deaminase (CD). Any cells that express CD and are subsequently exposed to fluorocytosine (5-FC) are killed; CD converts systemically administered 5-FC to the active anti-cancer agent 5-fluorouracil (5-FU), which is further converted to 5-fluorouracil triphosphate that interferes with RNA processing and irreversibly inhibits DNA synthesis[32, 33]. While other suicide gene approaches exist, including the thymidine kinase/ganciclovir approach, previous published studies have presented evidence the anti-cancer effects of CD/5-FC approach may outperform the other approaches in multiple tumors types[34-37]. 5-FC can be directly applied to cultured cells transfected with CD vectors or deliver 5-FC systemically to GBM PDX mice treated with DNP targeted to gliomas and containing plasmids encoding for CD.

Net, the methods can be carried out using a synthetic DNA nanoparticle designed to target two highly upregulated cell surface mechanisms on glioma that will increase particle uptake and enhance gene delivery specifically to tumors. To further reduce off-target effects, plasmid DNA can be designed to encode for a suicide gene that is under transcriptional control of a tumor-specific promoter. While the suicide gene approach is a tested approach in GBM studies, it is believed that this unique targeting approach combined with a gene therapy approach that restricts suicide gene expression specifically to tumor cells will improve upon what has already been reported for this approach. This combined approach should allow cancer-selective delivery of therapeutic nucleic acids, leading to a highly effective and safe gene therapy for GBM.

Figure 2:
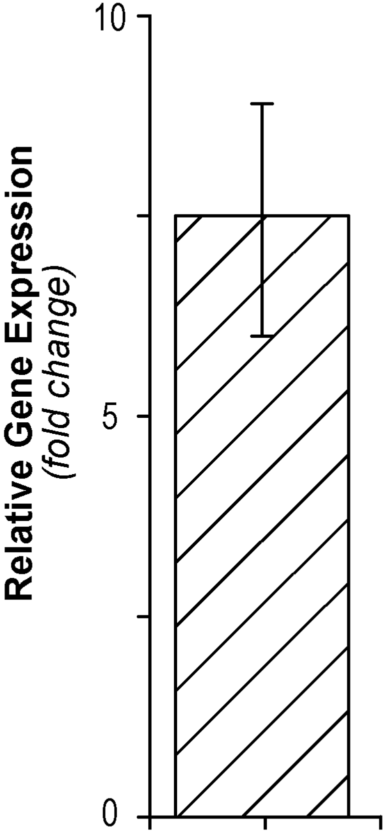
FIG. 2. Relative gene expression of nucleolin in cultures of U87 cells relative to human astrocytes. U87 cells show >7-fold higher levels of nucleolin expression.

It has been shown that the shuttle protein, nucleolin, played an important role for internalizing DNP into the cells and their subsequent transport to the nucleus[10]. FIG. 1 shows a diagram of the putative steps involved with DNP trafficking; as Chen et al.[10] reported, inhibiting cell surface nucleolin resulted in a strong reduction of DNP transfection efficiency. Several studies have reported that cell surface nucleolin is highly over-expressed in tumors in general[11] and gliomas in particular[12, 13]. Preliminary RT-PCR measures of nucleolin mRNA expression in cultures of human astrocytes or human U87 glioma cells by Applicant determined relatively higher expression in U87 cells (FIG. 2). It has further been determined that Fn14, the receptor for TWEAK, is highly upregulated in glioma. One such study using immunohistochemical (IHC) analysis of Fn14 in gliomas determined that 94%, 88% and 100% of cells in the core, edge and rim, respectively, had strong Fn14 expression[38]. Applicant has found in vitro that Fn14 (TWEAKR) is strongly expressed on U87 glioma cells using IHC staining for this receptor. Applicant has looked at Fn14 using IHC techniques in both normal human astrocytes and the U87 cell line. FIG. 3 is a confocal image of a U87 cell immunolabeled for Fn14. Rotation of this confocal image shows strong immunolabeling on the cell surface and within the cytoplasm. Fn14 immunostaining was barely detectable on normal human astrocytes.

Figure 4:
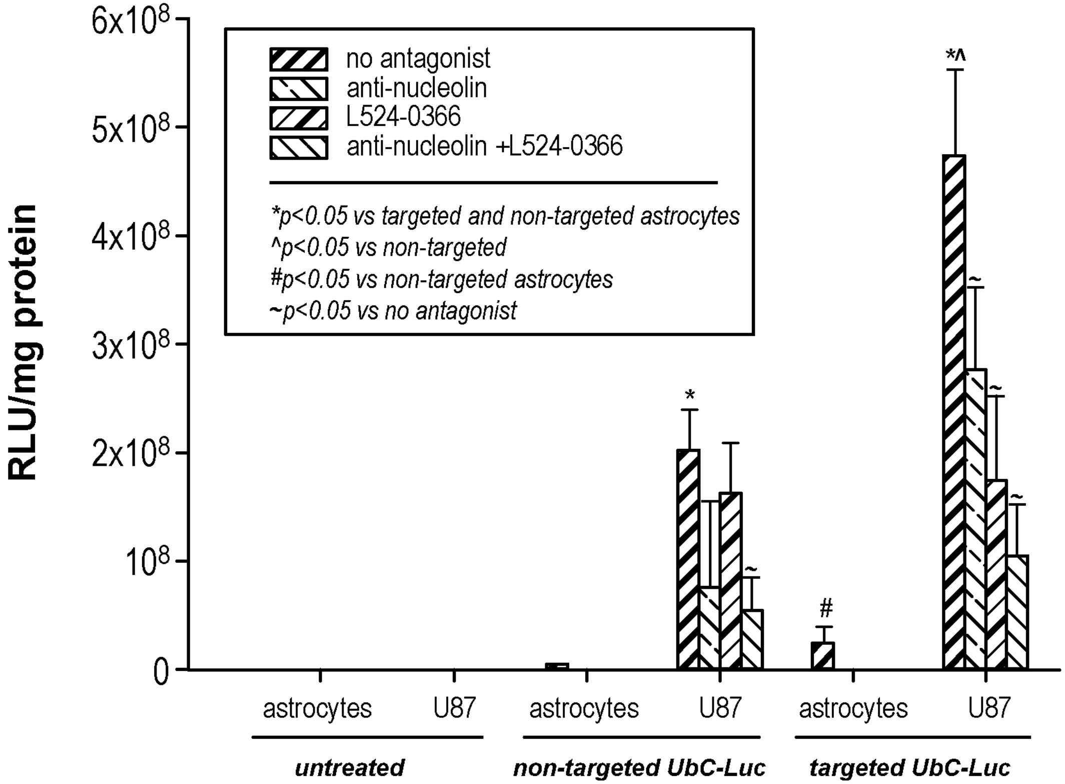
FIG. 4. Luciferase expression in cell lysates from human astrocyte or U87 glioma cultures. Cells were transfected with tDNP-TWEAK2 or ntDNP containing the UbC-Luc plasmid; untreated cells did not receive any DNP. Some U87 cultures were also treated with nucleolin antibody, L524-0366 (Fn14 antagonist) or a combination of both; astrocyte cultures were not treated with receptor antagonists.

Applicant has treated cultures of U87 cells and normal human astrocytes with targeted DNP (tDNP) or non-targeted DNP (ntDNP) containing plasmids encoding for the reporter gene luciferase under transcriptional control of the non-specific ubiquitin C promoter (UbC-Luc). Cells were transfected for a 3-day period with these DNP and luciferase activity was quantified. Luciferase expression in U87 cells transfected with targeted DNP was >20-fold higher than in astrocytes receiving the same treatment (FIG. 4); the relative increase between astrocytes and U87 for ntDNP most likely was due to the upregulation of nucleolin (FIG. 2). Competition studies in which receptor antagonists were added to U87 cultures at the time of DNP transfection were performed and we observed significant reductions in transgene expression as a result of blocking these two receptors (FIG. 4).

DNP Synthesis: As an example, PEG-CK30 DNA nanoparticles were used to demonstrate the efficacy of targeting the TWEAKR for gene delivery. Exemplary nanoparticle include those referenced in, for example: Liu G, Li D, Pasumarthy M K, Kowalczyk T H, Gedeon C R, Hyatt S L, Payne J M, Miller T J, Brunovskis P, Fink T L, Muhammad O, Moen R C, Hanson R W, Cooper M J. Nanoparticles of compacted DNA transfect postmitotic cells. J Biol Chem. 2003 Aug. 29; 278(35):32578-86. Epub 2003 Jun. 14. PubMed PMID: 12807905; Ziady A G, Gedeon C R, Miller T, Quan W, Payne J M, Hyatt S L, Fink T L, Muhammad O, Oette S, Kowalczyk T, Pasumarthy M K, Moen R C, Cooper M J, Davis P B. Transfection of airway epithelium by stable PEGylated poly-L-lysine DNA nanoparticles in vivo. Mol Ther. 2003 December; 8(6):936-47. PubMed PMID: 14664796; Ziady A G, Gedeon C R, Muhammad O, Stillwell V, Oette S M, Fink T L, Quan W, Kowalczyk T H, Hyatt S L, Payne J, Peischl A, Seng J E, Moen R C, Cooper M J, Davis P B Minimal toxicity of stabilized compacted DNA nanoparticles in the murine lung. Mol Ther. 2003 December; 8(6):948-56. PubMed PMID: 14664797; Konstan M W, Davis P B, Wagener J S, Hilliard K A, Stern R C, Milgram L J, Kowalczyk T H, Hyatt S L, Fink T L, Gedeon C R, Oette S M, Payne J M, Muhammad O, Ziady A G, Moen R C, Cooper M J. Compacted DNA nanoparticles administered to the nasal mucosa of cystic fibrosis subjects are safe and demonstrate partial to complete cystic fibrosis transmembrane regulator reconstitution. Hum Gene Ther. 2004 December; 15(12):1255-69. PubMed PMID: 15684701; Yurek D M, Fletcher A M, Smith G M, Seroogy K B, Ziady A G, Molter J, Kowalczyk T H, Padegimas L, Cooper M J. Long-term transgene expression in the central nervous system using DNA nanoparticles. Mol Ther. 2009 April; 17(4): 641-50. doi:10.1038/mt.2009.2. Epub 2009 Feb. 17. PubMed PMID: 19223866; PubMed Central PMCID: PMC2835115; Chen X, Kube D M, Cooper M J, Davis P B. Cell surface nucleolin serves as receptor for DNA nanoparticles composed of pegylated polylysine and DNA. Mol Ther. 2008 February; 16(2):333-42. Epub 2007 Dec. 4. PubMed PMID: 18059369; Yurek D M, Flectcher A M, Kowalczyk T H, Padegimas L, Cooper M J. Compacted DNA nanoparticle gene transfer of GDNF to the rat striatum enhances the survival of grafted fetal dopamine neurons. Cell Transplant. 2009; 18(10):1183-96. doi:10.3727/096368909X12483162196881. Epub 2009 Jun. 22. PubMed PMID: 19650971; PubMed Central PMCID: PMC3031110; Yurek D M, Fletcher A M, McShane M, Kowalczyk T H, Padegimas L, Weatherspoon M R, Kaytor M D, Cooper M J, Ziady A G. DNA nanoparticles: detection of long-term transgene activity in brain using bioluminescence imaging Mol Imaging. 2011 October; 10(5):327-39. doi: 10.2310/7290.2010.00053. Epub 2011 Apr. 27. PubMed PMID: 21521549; PubMed Central PMCID: PMC3173525; and Chen X, Shank S, Davis P B, Ziady A G. Nucleolin-mediated cellular trafficking of DNA nanoparticle is lipid raft and microtubule dependent and can be modulated by glucocorticoid. Mol Ther. 2011 January; 19(1):93-102. doi: 10.1038/mt.2010.214. Epub 2010 Oct. 19. PubMed PMID: 20959809; PubMed Central PMCID: PMC3017445. DNA nanoparticles comprising a CpG-depleted plasmid expressing the gene of interest (luciferase, eGFP or cytosine deaminase) under transcriptional control of a non-specific (ubiquitin C) or glioma-specific (survivin, hTERT, PEG-3 or nestin) promoter compacted with either targeted or non-targeted PEG-CK30, a PEGylated lysine polymer containing 30 lysine and 1 cysteine residues were constructed. The lysine residues allow the polymer to ionically interact with the phosphate backbone of the plasmid and compact DNA in to rod or toroid like nanoparticles. The PEG-CK30 polymers may be a synthesized conjugation of a 10 kDa PEG and the cysteine residue of a CK30 polymer. Targeted PEG-CK30 is synthesized similarly using a bifunctional 10 kDa PEG which is reacted with equimolar amounts of CK30 and the desired targeting moiety. Two targeting moieties are used for this study: TWEAK protein, which targets Fn14, and a C105Y ligand, which targets the serpin-enzyme complex receptor (SEC-R); for these studies C105Y serves as a negative control target moiety (SEC-R is highly expressed in lung and low expression in brain). DNP are compacted with purified conjugate. One non-targeted (ntDNP) and four targeted [two TWEAK moieties per DNP (tDNP-TWEAK2), ten TWEAK moieties per DNP (tDNP-TWEAK10), two C105Y ligands per DNP (tDNP-CY2), and ten C105Y ligands per DNP (tDNP-CY10)] per formulation. Adding additional binding moieties may result in increased uptake and transfection. To compact the DNP, plasmids are added dropwise to an agitated solution of the targeted and/or non-targeted PEG-CK30 and allowed to mix for 30 min. While not intending to be limited by the disclosure, in certain aspects, the plasmid may be compacted at an N/P ratio of 2, or 2 primary amines from the CK30 polymer per phosphate group of the plasmid. All DNP are compacted using the same procedure, while the amounts of targeted and non-targeted PEG-CK30 varied for each DNP. For example, plasmid encoding luciferase contains approximately 7740 phosphate groups which allow a minimum of 258 PEG-CK30 polymers to interact with a single plasmid. In the case of two TWEAK moieties per DNP, two polymers contained TWEAK-PEG-CK30 and 256 polymers contained non-targeted PEG-CK30. Following compaction, DNP are filtered through a 0.22 μm filter and the solvent exchanged to isotonic (0.9%) saline; for some studies, DNP may be suspended in hypertonic (3.0%) saline.

Example 2

A virus may be engineered or conjugated to express a TWEAK molecules (i.e., a TWEAKR binding sequence) on the surface of the viral capsid. For example, for the retargeting of a viral capsid to the TWEAKR, the coding sequence for TWEAK or a portion thereof may be included in the coding sequence for the capsid for the virus using methods known in the art such that TWEAK or a portion thereof (that binds to TWEAKR) is expressed as part of the capsid viral coat during generation of the a viral vector.

Alternatively, intact viral particles can be conjugated by conjugation chemistry, also using methods known in the art, to the TWEAK molecule or a portion of the TWEAK molecule (that binds to TWEAKR) such that TWEAK "decorates" the viral capsid and can be presented to cells during viral interaction with cells.

TWEAK containing viral particles (either by integration into the viral capsid genome or by conjugation) can be used to target cells that express TWEAKR, which may then be useful for the expansion of the tropisms of viral gene therapy vectors that otherwise may not bind such cells. For example, TWEAK conjugated viral vectors can be used to deliver a suicide gene to glioma cells to eliminate the tumor following IV or direct injection.

Example 3

In other aspects, liposomal nucleic acid vectors can be conjugated to TWEAK protein or a TWEAKR binding portion thereof. For example, conjugation chemistry (e.g. sulfhydryl or maleimide reactive groups) can be used to conjugate TWEAK or a TWEAKR binding region of TWEAK to a cationic liposome that can complex with nucleic acids to generate liposomal nucleic acid particles that can target TWEAKR expressing cells for gene delivery. For example, TWEAK conjugated liposomal vectors can be used to deliver a suicide gene to glioma cells to eliminate the tumor following IV or direct injection.

REFERENCES CITED

1. Schwartzbaum, J. A., et al., Epidemiology and molecular pathology of glioma. Nat Clin Pract Neurol, 2006. 2(9): p. 494-503; quiz 1 p following 516.
2. Yabroff, K. R., et al., Patterns of care and survival for patients with glioblastoma multiforme diagnosed during 2006. Neuro Oncol, 2012. 14(3): p. 351-9.
3. O'Mahony, A. M., et al., Non-viral nanosystems for gene and small interfering RNA delivery to the central nervous system: formulating the solution. J Pharm Sci, 2013. 102(10): p. 3469-84.
4. Tobias, A., et al., The art of gene therapy for glioma: a review of the challenging road to the bedside. J Neurol Neurosurg Psychiatry, 2013. 84(2): p. 213-22.
5. Assi, H., et al., Gene therapy for brain tumors: basic developments and clinical implementation. Neurosci Lett, 2012. 527(2): p. 71-7.
6. Yurek, D., et al., Intracerebral injections of DNA nanoparticles encoding for a therapeutic gene provide partial neuroprotection in an animal model of neurodegeneration. Nanomedicine, 2017. 13(7): p. 2209-2217.
7. Yurek, D. M., et al., Long-term transgene expression in the central nervous system using DNA nanoparticles. Mol Ther, 2009. 17(4): p. 641-50.
8. Yurek, D. M., et al., DNA nanoparticles: detection of long-term transgene activity in brain using bioluminescence imaging. Mol Imaging, 2011. 10(5): p. 327-39.
9. Yurek, D. M., et al., Age and lesion-induced increases of GDNF transgene expression in brain following intracerebral injections of DNA nanoparticles. Neuroscience, 2015. 284: p. 500-12.
10. Chen, X., et al., Cell surface nucleolin serves as receptor for DNA nanoparticles composed of pegylated polylysine and DNA. Mol Ther, 2008. 16(2): p. 333-42.
11. Soundararajan, S., et al., Plasma membrane nucleolin is a receptor for the anticancer aptamer AS1411 in MV4-11 leukemia cells. Mol Pharmacol, 2009. 76(5): p. 984-91.
12. Galzio, R., et al., Glycosilated nucleolin as marker for human gliomas. J Cell Biochem, 2012. 113(2): p. 571-9.
13. Xu, Z., et al., Knocking down nucleolin expression in gliomas inhibits tumor growth and induces cell cycle arrest. J Neurooncol, 2012. 108(1): p. 59-67.
14. Winkles, J. A., The TWEAK-Fn14 cytokine-receptor axis: discovery, biology and therapeutic targeting. Nat Rev Drug Discov, 2008. 7(5): p. 411-25.
15. Bossen, C., et al., Interactions of tumor necrosis factor (TNF) and TNF receptor family members in the mouse and human J Biol Chem, 2006. 281(20): p. 13964-71.
16. Li, A., et al., Unsupervised analysis of transcriptomic profiles reveals six glioma subtypes. Cancer Res, 2009. 69(5): p. 2091-9.
17. Shirahata, M., et al., Gene expression-based molecular diagnostic system for malignant gliomas is superior to histological diagnosis. Clin Cancer Res, 2007. 13(24): p. 7341-56.
18. Shirahata, M., et al., Using gene expression profiling to identify a prognostic molecular spectrum in gliomas. Cancer Sci, 2009. 100(1): p. 165-72.
19. Tran, N. L., et al., The human Fn14 receptor gene is up-regulated in migrating glioma cells in vitro and overexpressed in advanced glial tumors. Am J Pathol, 2003. 162(4): p. 1313-21.
20. Pelekanou, V., et al., BAFF, APRIL, TWEAK, BCMA, TACI and Fn14 proteins are related to human glioma tumor grade: immunohistochemistry and public microarray data meta-analysis. PLoS One, 2013. 8(12): p. e83250.
21. Tran, N. L., et al., Increased fibroblast growth factor-inducible 14 expression levels promote glioma cell invasion via Rac1 and nuclear factor-kappaB and correlate with poor patient outcome. Cancer Res, 2006. 66(19): p. 9535-42.
22. Phillips, H. S., et al., Molecular subclasses of high-grade glioma predict prognosis, delineate a pattern of disease progression, and resemble stages in neurogenesis. Cancer Cell, 2006. 9(3): p. 157-73.
23. Gurunathan, S., et al., Regulation of fibroblast growth factor-inducible 14 (Fn14) expression levels via ligand-independent lysosomal degradation. J Biol Chem, 2014. 289(19): p. 12976¬88.
24. Zhou, H., et al., Development of human serine protease-based therapeutics targeting Fn14 and identification of Fn14 as a new target overexpressed in TNBC. Mol Cancer Ther, 2014. 13(11): p. 2688-705.
25. Perez, J. G., et al., The TWEAK receptor Fn14 is a potential cell surface portal for targeted delivery of glioblastoma therapeutics. Oncogene, 2016. 35(17): p. 2145-55.
26. Altieri, D. C., Validating survivin as a cancer therapeutic target. Nat Rev Cancer, 2003. 3(1): p. 46-54.
27. Kajiwara, Y., et al., Expression of survivin in astrocytic tumors: correlation with malignant grade and prognosis. Cancer, 2003. 97(4): p. 1077-83.
28. Fan, X., et al., hTERT gene amplification and increased mRNA expression in central nervous system embryonal tumors. Am J Pathol, 2003. 162(6): p. 1763-9.
29. Bhang, H. E., et al., Tumor-specific imaging through progression elevated gene-3 promoter-driven gene expression. Nat Med, 2011. 17(1): p. 123-9.
30. Jiang, X., et al., The imprinted gene PEGS inhibits Wnt signaling and regulates glioma growth. J Biol Chem, 2010. 285(11): p. 8472-80.
31. Arai, H., et al., Nestin expression in brain tumors: its utility for pathological diagnosis and correlation with the prognosis of high-grade gliomas. Brain Tumor Pathol, 2012. 29(3): p. 1607.
32. Portsmouth, D., J. Hlavaty, and M. Renner, Suicide genes for cancer therapy. Mol Aspects Med, 2007. 28(1): p. 4-41.
33. Zarogoulidis, P., et al., Suicide Gene Therapy for Cancer—Current Strategies. J Genet Syndr Gene Ther, 2013. 4.
34. Dachs, G. U., J. Tupper, and G. M. Tozer, From bench to bedside for gene-directed enzyme prodrug therapy of cancer. Anticancer Drugs, 2005. 16(4): p. 349-59.
35. Shirakawa, T., et al., Cytotoxicity of adenoviral-mediated cytosine deaminase plus 5-fluorocytosine gene therapy is superior to thymidine kinase plus acyclovir in a human renal cell carcinoma model. J Urol, 1999. 162(3 Pt 1): p. 949-54.
36. Trinh, Q. T., et al., Enzyme/prodrug gene therapy: comparison of cytosine deaminase/5-fluorocytosine versus thymidine kinase/ganciclovir enzyme/prodrug systems in a human colorectal carcinoma cell line. Cancer Res, 1995. 55(21): p. 4808-12.

37. Zhang, J., V. Kale, and M. Chen, Gene-directed enzyme prodrug therapy. AAPS J, 2015. 17(1): p. 102-10.
38. Fortin, S. P., et al., Tumor necrosis factor-like weak inducer of apoptosis stimulation of glioma cell survival is dependent on Akt2 function. Mol Cancer Res, 2009. 7(11): p. 1871-81.
39. Negroni, L., et al., Treatment of colon cancer cells using the cytosine deaminase/5-fluorocytosine suicide system induces apoptosis, modulation of the proteome, and Hsp90beta phosphorylation. Mol Cancer Ther, 2007. 6(10): p. 2747-56.
40. Kibbey, M. C., et al., A 110-kD nuclear shuttling protein, nucleolin, binds to the neurite-promoting IKVAV site of laminin-1 J Neurosci Res, 1995. 42(3): p. 314-22.
41. Martens, T., et al., Inhibition of glioblastoma growth in a highly invasive nude mouse model can be achieved by targeting epidermal growth factor receptor but not vascular endothelial growth factor receptor-2. Clin Cancer Res, 2008. 14(17): p. 5447-58.
42. Sausville, E. A. and A. M. Burger, Contributions of human tumor xenografts to anticancer drug development. Cancer Res, 2006. 66(7): p. 3351-4, discussion 3354.
43. Taillandier, L., L. Antunes, and K. S. Angioi-Duprez, Models for neuro-oncological preclinical studies: solid orthotopic and heterotopic grafts of human gliomas into nude mice. J Neurosci Methods, 2003. 125(1-2): p. 147-57.
44. Joo, K. M., et al., Patient-specific orthotopic glioblastoma xenograft models recapitulate the histopathology and biology of human glioblastomas in situ. Cell Rep, 2013. 3(1): p. 260-73.
45. Patrizii, M., et al., Utility of Glioblastoma Patient-Derived Orthotopic Xenografts in Drug Discovery and Personalized Therapy. Front Oncol, 2018. 8: p. 23.
46. Xu, Z., et al., Orthotopic Patient-Derived Glioblastoma Xenografts in Mice. Methods Mol Biol, 2018. 1741: p. 183-190.
47. Ostrom, Q. T., et al., CBTRUS statistical report: Primary brain and central nervous system tumors diagnosed in the United States in 2006-2010. Neuro Oncol, 2013. 15 Suppl 2: p. ii1-56.
48. Ndesendo, V. M., Convection-Enhanced Delivery of Neurotherapeutics, in Advances in Neurotherapeutic Delivery Technologies, V. PIllay and C. Y. E., Editors. 2015, OMICS Group: Foster City, CA. p. 3-23.
49. Saucier-Sawyer, J. K., et al., Distribution of polymer nanoparticles by convection-enhanced delivery to brain tumors. J Control Release, 2016. 232: p. 103-12.
50. Vogelbaum, M. A. and M. K. Aghi, Convection-enhanced delivery for the treatment of glioblastoma. Neuro Oncol, 2015. 17 Suppl 2: p. ii3-ii8.
51. Mastorakos, P., et al., Highly PEGylated DNA Nanoparticles Provide Uniform and Widespread Gene Transfer in the Brain. Adv Healthc Mater, 2015. 4(7): p. 1023-33.
52. Neeves, K. B., et al., Dilation and degradation of the brain extracellular matrix enhances penetration of infused polymer nanoparticles. Brain Res, 2007. 1180: p. 121-32.
53. Nance, E. A., et al., A dense poly(ethylene glycol) coating improves penetration of large polymeric nanoparticles within brain tissue. Sci Transl Med, 2012. 4(149): p. 149ra119.
54. Christensen, C. L., et al., Targeted cytosine deaminase-uracil phosphoribosyl transferase suicide gene therapy induces small cell lung cancer-specific cytotoxicity and tumor growth delay. Clin Cancer Res, 2010. 16(8): p. 2308-19.
55. Redgate, E. S., M. Deutsch, and S. S. Boggs, Time of death of CNS tumor-bearing rats can be reliably predicted by body weight-loss patterns. Lab Anim Sci, 1991. 41(3): p. 269-73.
56. Workman, P., et al., Guidelines for the welfare and use of animals in cancer research. Br J Cancer, 2010. 102(11): p. 1555-77.
57. Mead, B. P., et al., Novel Focused Ultrasound Gene Therapy Approach Noninvasively Restores Dopaminergic Neuron Function in a Rat Parkinson's Disease Model. Nano Lett, 2017. 17(6): p. 3533-3542.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. All accessioned information (e.g., as identified by PUBMED, PUBCHEM, NCBI, UNIPROT, or EBI accession numbers) and publications in their entireties are incorporated into this disclosure by reference in order to more fully describe the state of the art as known to those skilled therein as of the date of this disclosure. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A method of treating a glioblastoma, comprising administering to an individual in need thereof a composition comprising a DNA nanoparticle (DNP); the DNP comprising a 30-mer lysine polymer substituted with polyethylene glycol, wherein the polyethylene glycol has a molecular weight of 10 kDa;

a protein or peptide ligand having at least 90% sequence identity to a TNF superfamily member 12 (TWEAK) protein and which is specific for TNF receptor superfamily member 12A ("TWEAKR"); wherein the protein or peptide ligand is conjugated to the DNP; and a plasmid comprising a suicide gene under the control of a glioma-cell specific promoter.

2. The method of claim 1, wherein the nanoparticle comprises at least two TWEAK protein or peptide ligands, or at least three TWEAK protein or peptide ligands, or at least four TWEAK protein or peptide ligands, or at least five TWEAK protein or peptide ligands, or at least six TWEAK protein or peptide ligands, or at least seven TWEAK protein or peptide ligands, or at least eight TWEAK protein or peptide ligands, or at least nine TWEAK protein or peptide ligands, or at least ten TWEAK protein or peptide ligands, or greater than at least 10 tweak protein or peptide ligands per nanoparticle.

3. The method of claim 1, wherein the suicide gene encodes a protein selected from caspase 9, caspase 3, caspase 7, thymidine kinase (TK), or cytosine deaminase (CD);

wherein AP1903 is administered if the protein is caspase 9, caspase 3, or caspase 7;

wherein ganciclovir is administered if the protein is TK; and wherein 5-flurocytosine (5-FC) is administered if the protein is CD.

4. The method of claim 1, wherein the promoter is selected from survivin, hTERT, PEG-3, nestin, or combinations thereof.

5. The method of claim 1, wherein the lysine polymer comprises at least one cysteine residue.

6. The method of claim 1, wherein the nanoparticle has a shape selected from rod, spheroid, or toroid-like shape.

7. The method of claim 1, wherein the composition comprises a hypertonic solution.

8. The method of claim 1, wherein the administering step is carried out via one or more administration routes selected from intravenous injection, intraperitoneal injection, intracranial, and intracerebral injection.

9. The method of claim 8, wherein the one or more administration routes comprises a direct injection into the site of tumor cells.

10. The method of claim 9, wherein the direct injection is carried out using convection enhanced delivery (CED).

11. The method of claim 10, wherein the CED bypasses the BBB by directly delivering the composition to a brain tumor.

12. The method of claim 1, further comprising treating said individual with irradiation prior to said administration.

* * * * *